US008529585B2

(12) United States Patent
Jacobs et al.

(10) Patent No.: US 8,529,585 B2
(45) Date of Patent: Sep. 10, 2013

(54) SURGICAL CLAMP AND SURGICAL CLAMP INSTALLATION TOOL

(75) Inventors: Moises Jacobs, Miami, FL (US); Jesus R. Armenteros, Santo Domingo (DO); Garrett Barker, Meridian, TX (US); C. Kenneth French, Cranfills Gap, TX (US)

(73) Assignee: Advanced Bariatric Technology, LLC, Coral Gables, FL (US)

( * ) Notice: Subject to any disclaimer, the term of this patent is extended or adjusted under 35 U.S.C. 154(b) by 284 days.

(21) Appl. No.: 13/017,666

(22) Filed: Jan. 31, 2011

(65) Prior Publication Data

US 2011/0190791 A1 Aug. 4, 2011

Related U.S. Application Data

(60) Provisional application No. 61/299,725, filed on Jan. 29, 2010.

(51) Int. Cl.
*A61B 17/10* (2006.01)

(52) U.S. Cl.
USPC ............ 606/139; 606/151; 606/158; 606/120

(58) Field of Classification Search
USPC ............... 600/29, 30, 37; 606/151, 139, 158, 606/191, 193, 198; 128/831, 843
See application file for complete search history.

(56) References Cited

U.S. PATENT DOCUMENTS 3,766,925 A * 10/1973 Rubricius .................. 606/120
4,390,019 A * 6/1983 LeVeen et al. ............. 606/158

(Continued)

FOREIGN PATENT DOCUMENTS

DE 19751733 A1 12/1998
EP 0201344 A2 11/1986

(Continued)

OTHER PUBLICATIONS

PCT International Search Report and Written Opinion cited in Patent Application No. PCT/US2011/023205, dated Apr. 5, 2011 (13 pages).

(Continued)

*Primary Examiner* — Vy Q Bui
(74) *Attorney, Agent, or Firm* — Gardere Wynne Sewell LLP

(57) ABSTRACT

A surgical clamp in certain embodiments may be configured to operate with a surgical installation tool. The clamp may have two elongated members with a bight portion that joins the two elongated members at a proximal end of the clamp and that may bias the two elongated members in an open position at a distal end. The bight portion may have one or more engagement features, such as a slotted aperture or other engagement or coupling feature. A clasp mechanism at the distal end of the clamp may have a male or first component disposed on or adjacent one of the two elongated members and a female or second component disposed on or adjacent the other of the two elongated members at the distal end of the clamp. The installation tool may include an elongated member with a proximal end and a distal end that has an engagement feature to engage the clamp, such as at the bight portion. A handle in one embodiment may be provided at the proximal end of the installation tool, while a head at the distal end may be configured to receive and/or engage the proximal end of the clamp and may also be operable to articulate in at least one plane.

13 Claims, 34 Drawing Sheets

(56) References Cited

U.S. PATENT DOCUMENTS

| | | | |
|---|---|---|---|
| 4,458,681 A | 7/1984 | Hopkins | |
| 4,558,699 A | 12/1985 | Bashour | |
| 4,803,985 A | 2/1989 | Hill | |
| 4,950,284 A | 8/1990 | Green et al. | |
| 4,976,721 A | 12/1990 | Blasnik et al. | |
| 5,074,868 A | 12/1991 | Kuzmak | |
| 5,163,945 A | 11/1992 | Ortiz et al. | |
| 5,226,429 A | 7/1993 | Kuzmak | |
| 5,234,454 A | 8/1993 | Bangs | |
| 5,236,437 A | 8/1993 | Wilk et al. | |
| 5,327,914 A | 7/1994 | Shlain | |
| 5,345,949 A | 9/1994 | Shlain | |
| 5,464,416 A | 11/1995 | Steckel | |
| 5,549,621 A | 8/1996 | Bessler et al. | |
| 5,575,802 A * | 11/1996 | McQuilkin et al. | 606/151 |
| 5,766,189 A | 6/1998 | Matsuno | |
| 6,179,850 B1 * | 1/2001 | Goradia | 606/158 |
| 6,464,710 B1 | 10/2002 | Foster | |
| 6,537,289 B1 | 3/2003 | Kayan et al. | |
| 6,572,629 B2 | 6/2003 | Kalloo et al. | |
| 6,694,982 B2 | 2/2004 | Latour | |
| 6,716,226 B2 | 4/2004 | Sixto, Jr. et al. | |
| 6,814,742 B2 | 11/2004 | Kimura et al. | |
| 6,869,438 B2 | 3/2005 | Chao | |
| 6,981,978 B2 | 1/2006 | Gannoe | |
| 7,022,126 B2 | 4/2006 | De Canniere | |
| 7,105,000 B2 | 9/2006 | McBrayer | |
| 7,135,032 B2 | 11/2006 | Akerfeldt | |
| 7,214,233 B2 | 5/2007 | Gannoe et al. | |
| 7,232,445 B2 | 6/2007 | Kortenbach et al. | |
| 7,261,725 B2 | 8/2007 | Binmoeller | |
| 7,288,100 B2 | 10/2007 | Molina Trigueros | |
| 7,338,503 B2 | 3/2008 | Rosenberg et al. | |
| 7,416,528 B2 | 8/2008 | Crawford et al. | |
| 7,645,285 B2 | 1/2010 | Cosgrove et al. | |
| 7,691,053 B2 | 4/2010 | Viola | |
| 7,758,493 B2 | 7/2010 | Gingras | |
| 7,871,416 B2 | 1/2011 | Phillips | |
| 7,892,244 B2 | 2/2011 | Monassevitch et al. | |
| 2002/0022851 A1 | 2/2002 | Kalloo et al. | |
| 2002/0138086 A1 | 9/2002 | Sixto et al. | |
| 2004/0097989 A1 | 5/2004 | Trigueros | |
| 2005/0119674 A1 | 6/2005 | Gingras | |
| 2005/0125014 A1 | 6/2005 | Duluco et al. | |
| 2005/0149069 A1 | 7/2005 | Bertolero et al. | |
| 2005/0197714 A1 | 9/2005 | Sayet | |
| 2005/0216042 A1 | 9/2005 | Gertner | |
| 2005/0277959 A1 | 12/2005 | Cosgrove et al. | |
| 2006/0074440 A1 | 4/2006 | Garner | |
| 2006/0157067 A1 | 7/2006 | Saadat et al. | |
| 2006/0217757 A1 | 9/2006 | Horndeski | |
| 2006/0252983 A1 | 11/2006 | Lembo et al. | |
| 2006/0264981 A1 | 11/2006 | Viola | |
| 2006/0264982 A1 | 11/2006 | Viola et al. | |
| 2007/0021761 A1 | 1/2007 | Phillips | |
| 2007/0032807 A1 | 2/2007 | Ortiz et al. | |
| 2007/0167962 A1 | 7/2007 | Gannoe et al. | |
| 2007/0213747 A1 | 9/2007 | Monassevitch et al. | |
| 2007/0265644 A1 | 11/2007 | Ichihara et al. | |
| 2008/0033457 A1 | 2/2008 | Francischelli et al. | |
| 2008/0039879 A1 | 2/2008 | Chin et al. | |
| 2008/0092910 A1 | 4/2008 | Brooks | |
| 2008/0177292 A1 | 7/2008 | Jacobs et al. | |
| 2008/0208324 A1 | 8/2008 | Glithero et al. | |
| 2008/0275480 A1 | 11/2008 | Jacobs et al. | |
| 2008/0287976 A1 | 11/2008 | Weaner et al. | |
| 2008/0319435 A1 | 12/2008 | Rioux et al. | |
| 2011/0190791 A1 | 8/2011 | Jacobs et al. | |

FOREIGN PATENT DOCUMENTS

| | | |
|---|---|---|
| EP | 1397998 A1 | 3/2004 |
| EP | 1547529 A1 | 6/2005 |
| EP | 1749506 A1 | 2/2007 |
| EP | 1806101 A1 | 7/2007 |
| EP | 1882451 A2 | 1/2008 |
| JP | 9289989 A | 11/1997 |
| JP | 2002085414 A | 3/2002 |
| JP | 2007044517 A | 2/2007 |
| JP | 2007097664 A | 4/2007 |
| JP | 2007159794 A | 6/2007 |
| WO | 2000076432 A1 | 12/2000 |
| WO | 2002064041 A1 | 8/2002 |
| WO | 2004017839 A1 | 3/2004 |
| WO | 2006033385 A1 | 3/2006 |
| WO | 2007013995 A2 | 2/2007 |
| WO | 2008081436 A2 | 7/2008 |
| WO | 2008091537 A2 | 7/2008 |
| WO | 2008101048 A2 | 8/2008 |
| WO | WO 2011/094700 | 8/2011 |

OTHER PUBLICATIONS

Helmut Kapczynski, Surgical Instruments 101, An Introduction to KMedic Certified Instruments, KMedic, Inc., 1997, Northvale, New Jersey (181 Pages).

PCT International Search Report cited in Patent Application No. PCT/US2008/000644, dated Jul. 7, 2008 (1 page).

Office Action cited in U.S. Appl. No. 11/797,537, dated Jul. 16, 2009 (10 pages).

Final Office Action cited in U.S. Appl. No. 11/797,537, dated Jan. 7, 2010 (9 pages).

Office Action cited in U.S. Appl. No. 11/984,452, dated Aug. 5, 2009 (13 pages).

Final Office Action cited in U.S. Appl. No. 11/984,452, dated Mar. 26, 2010 (11 pages).

Examiner's Interview Summary cited in U.S. Appl. No. 11/984,452, dated Jun. 11, 2010 (5 pages).

* cited by examiner

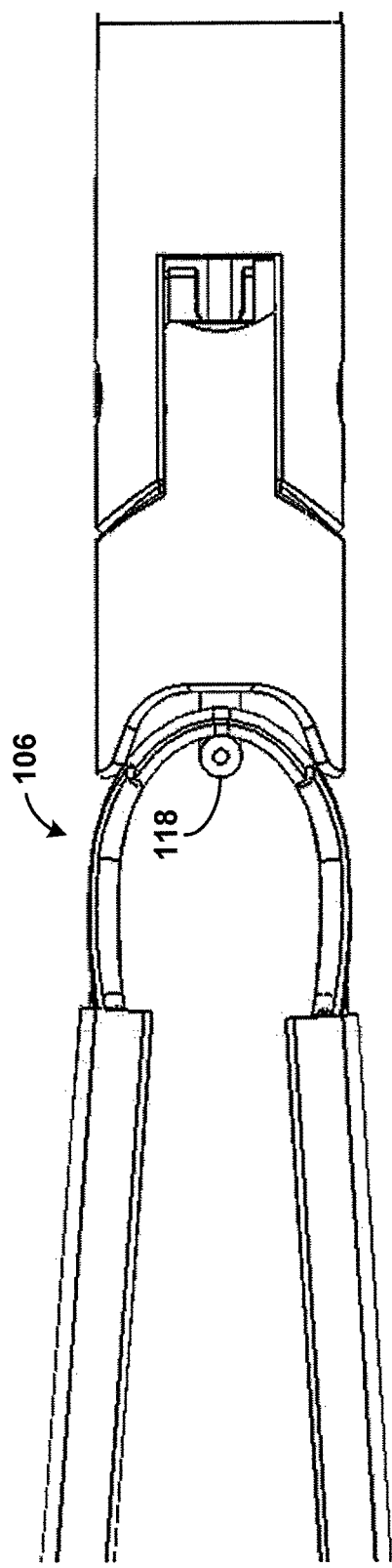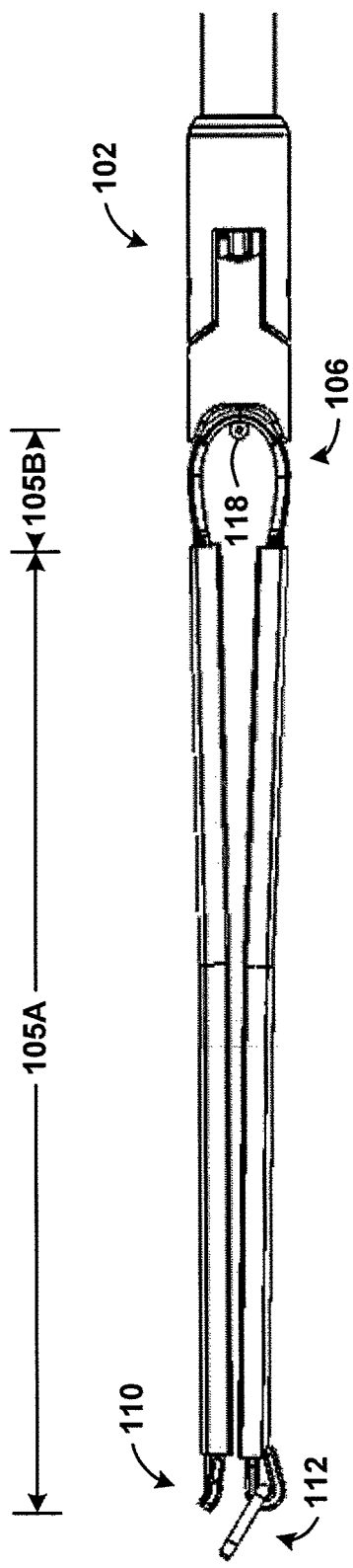
*Figure - 2(d)*
*Figure - 2(e)*

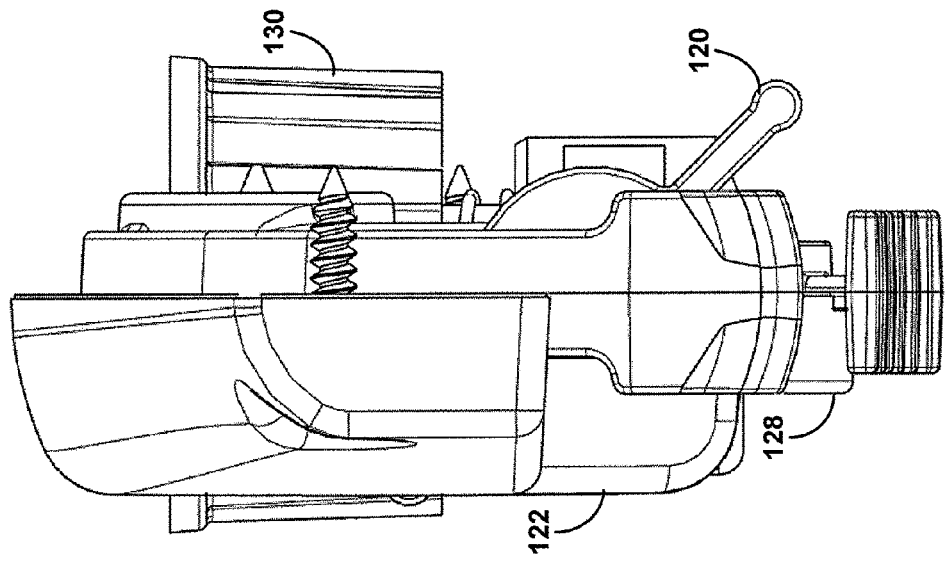
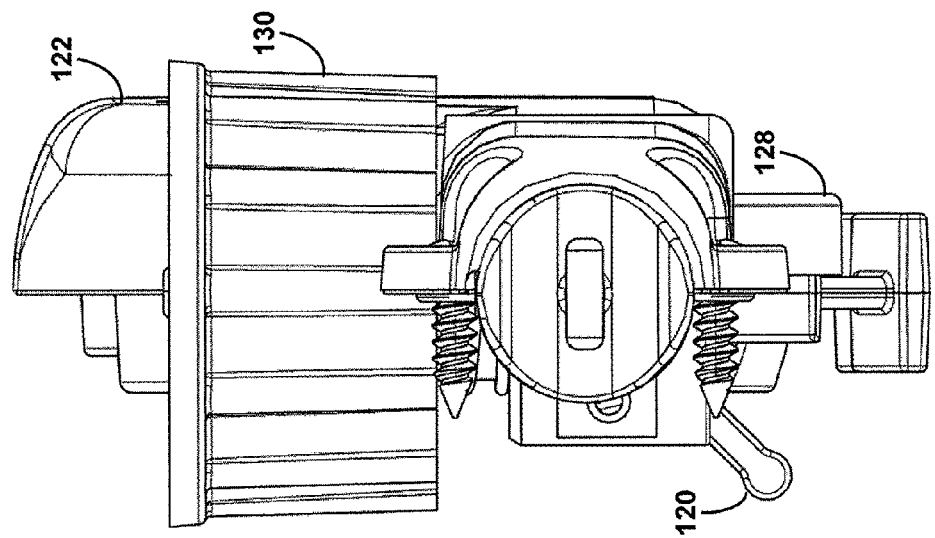

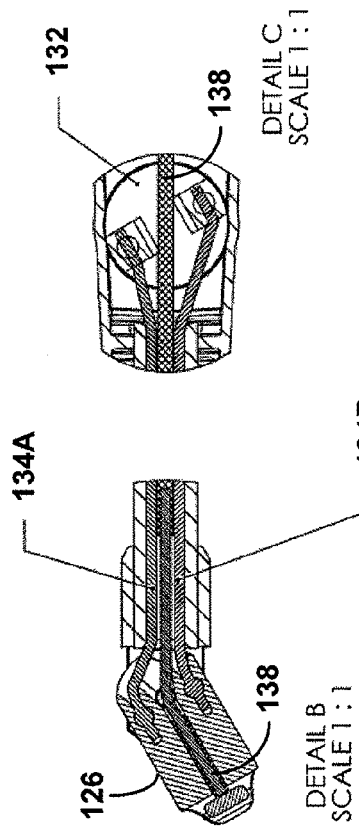
Figure - 4(e)
Figure - 4(d)
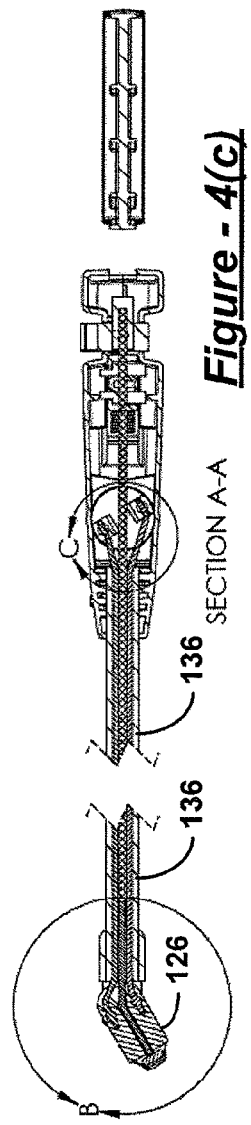
Figure - 4(c)
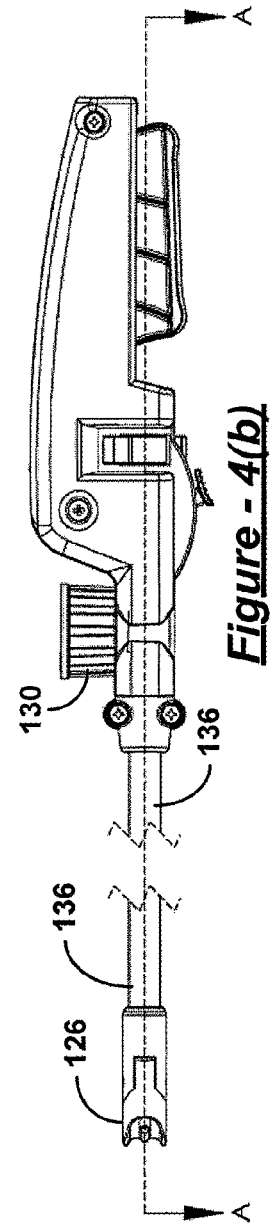
Figure - 4(b)

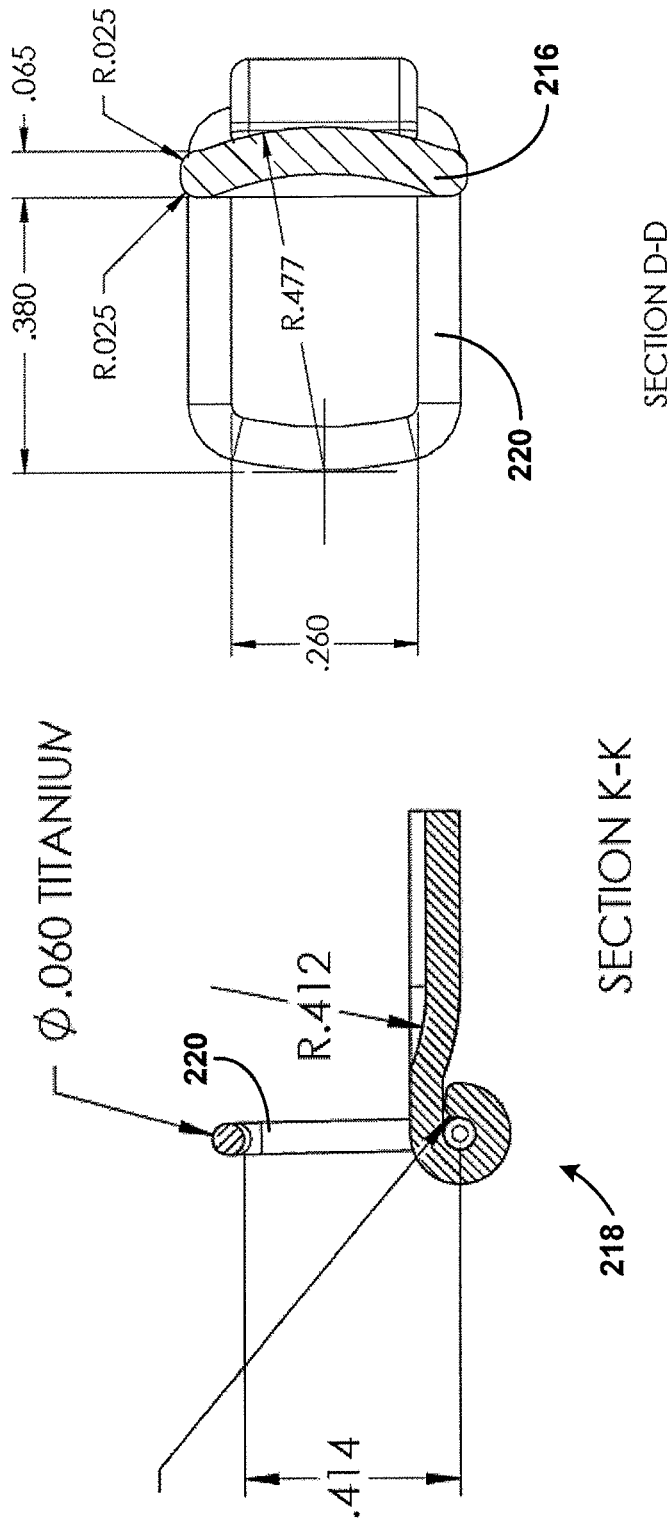

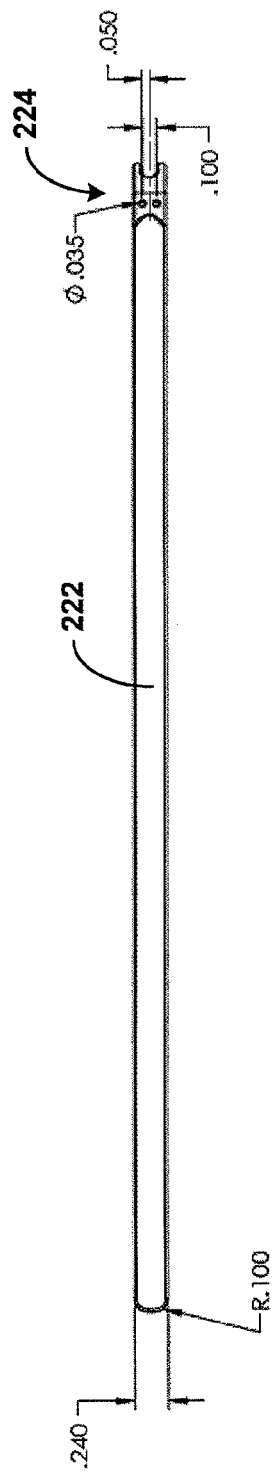
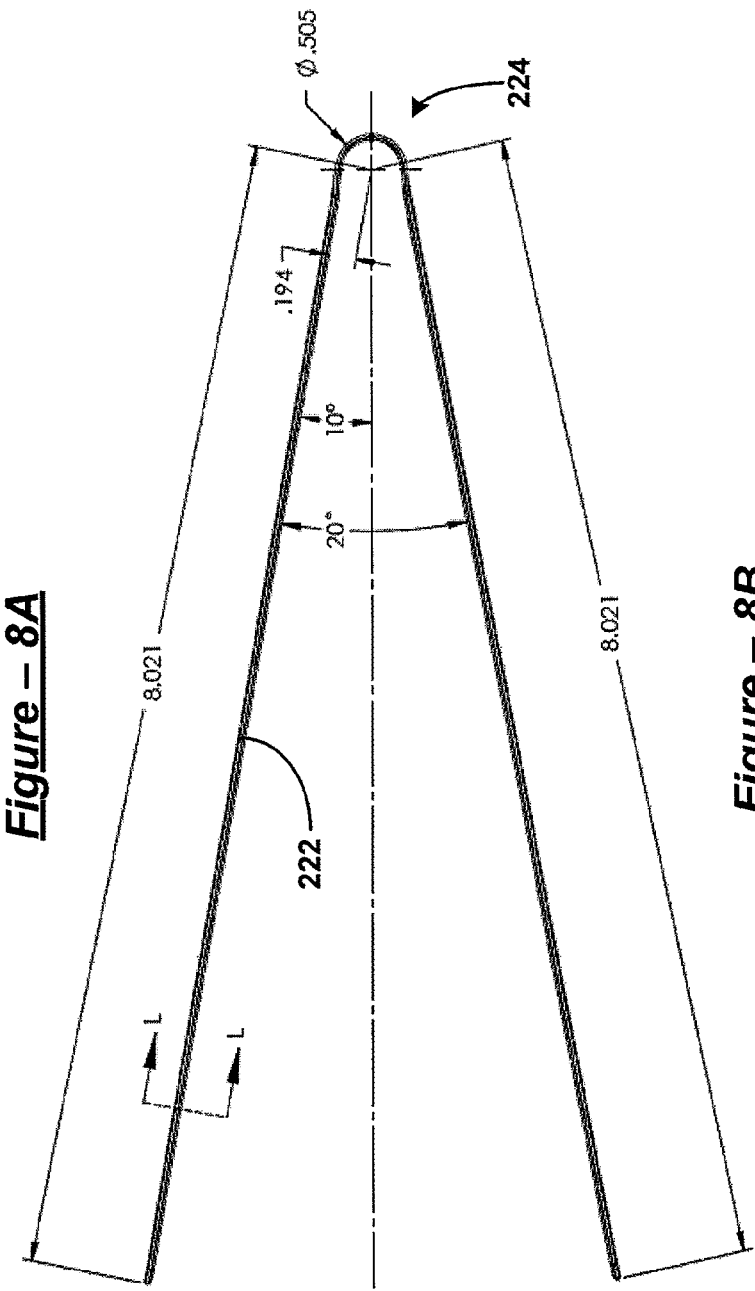
*Figure - 8A*
*Figure - 8B*

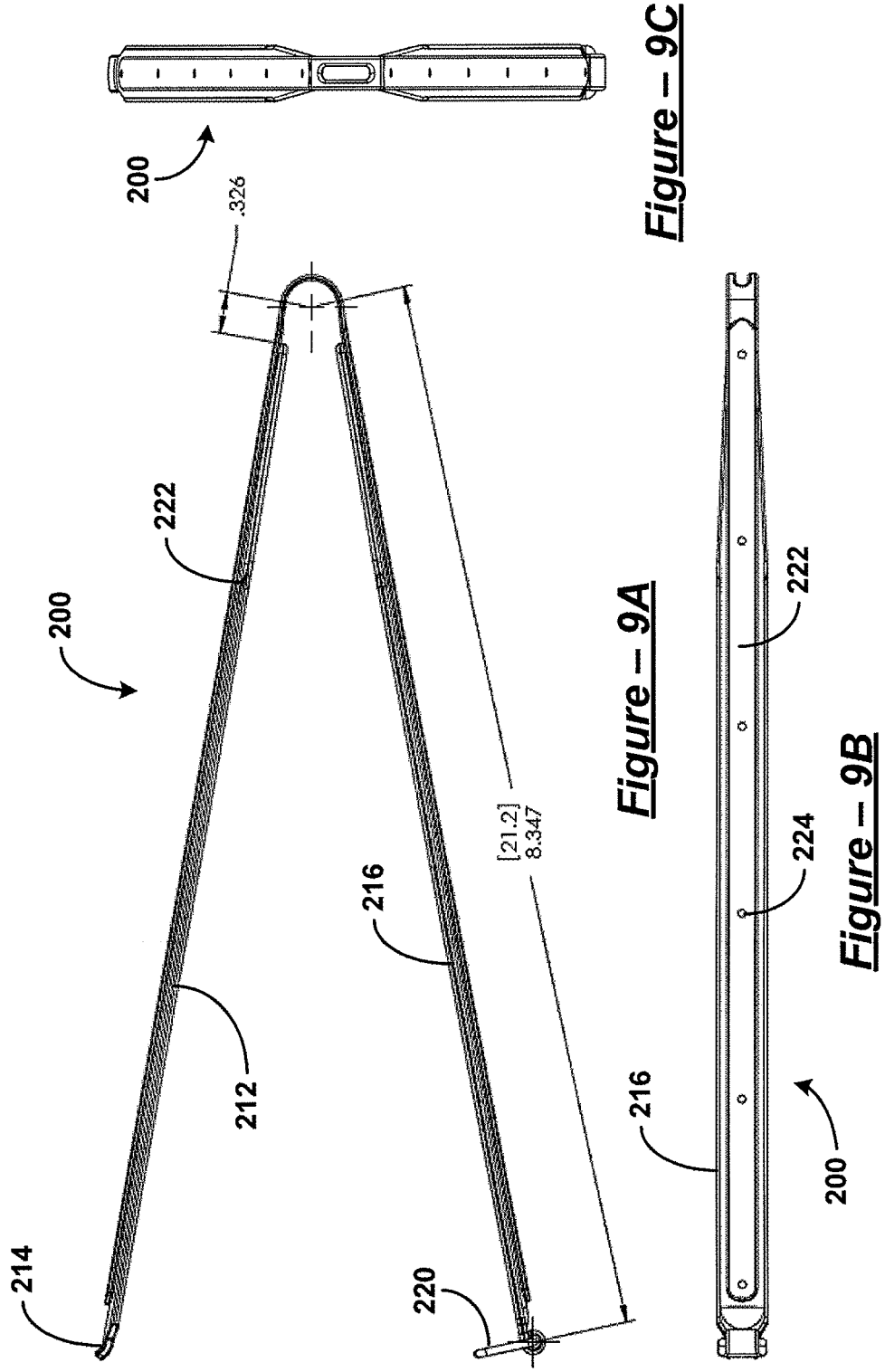

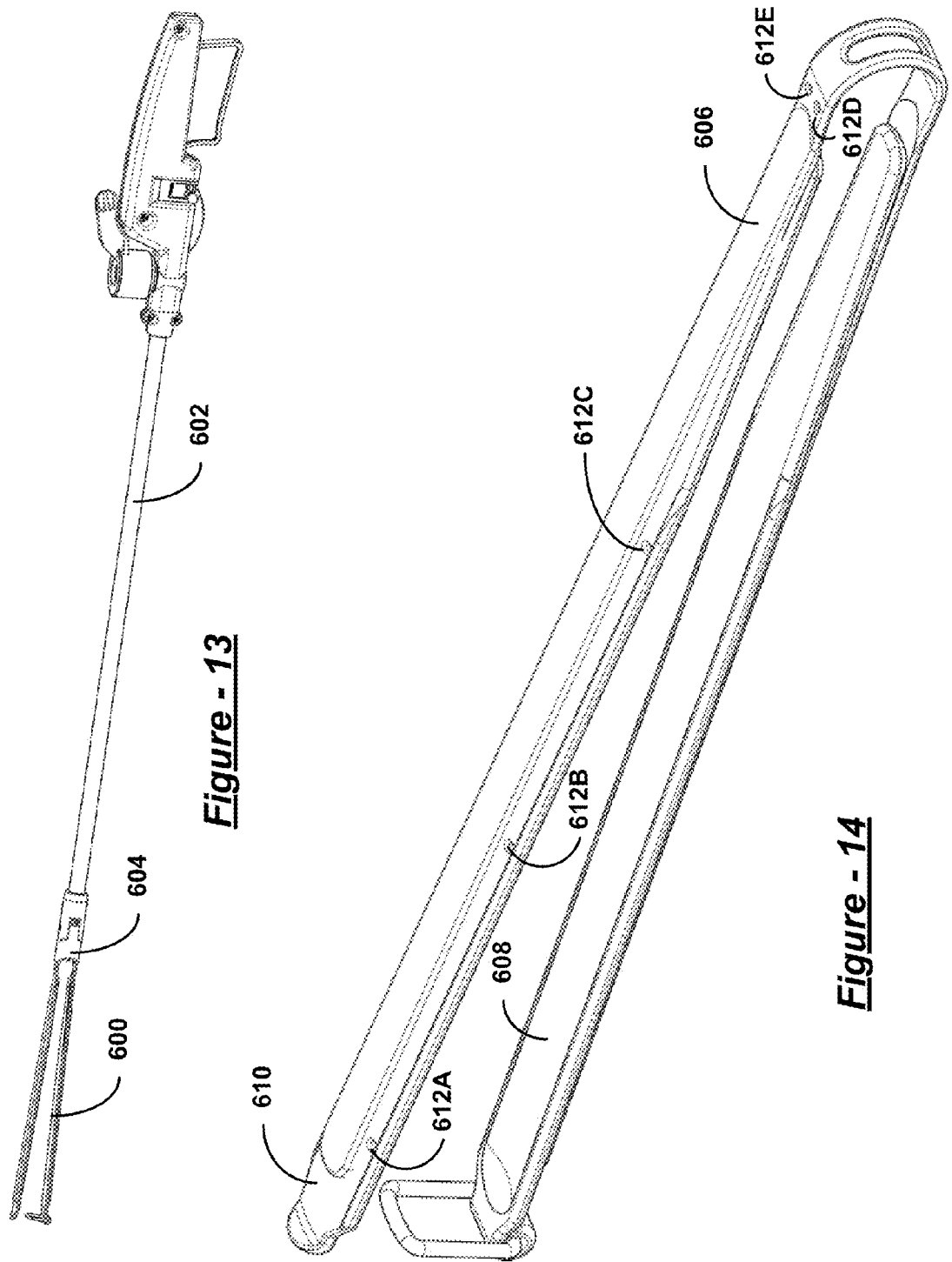

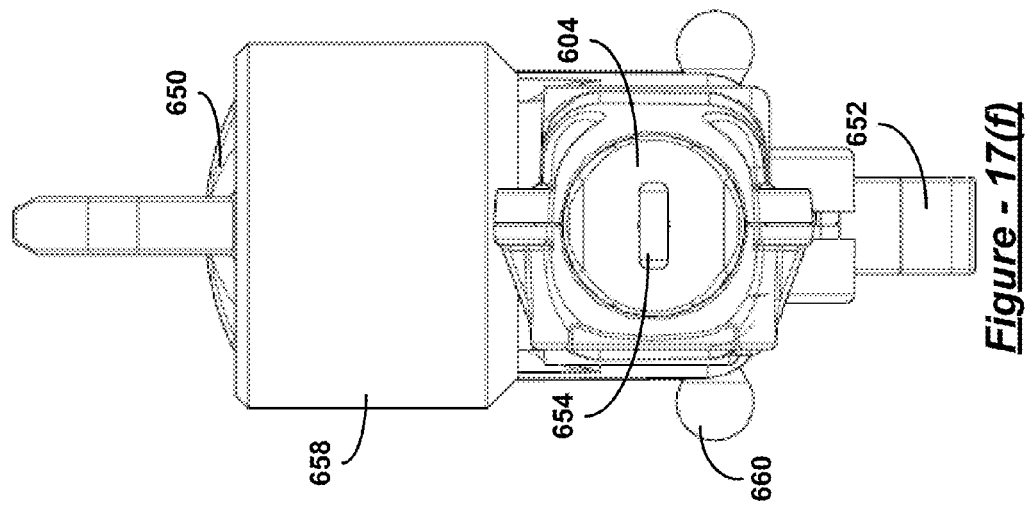
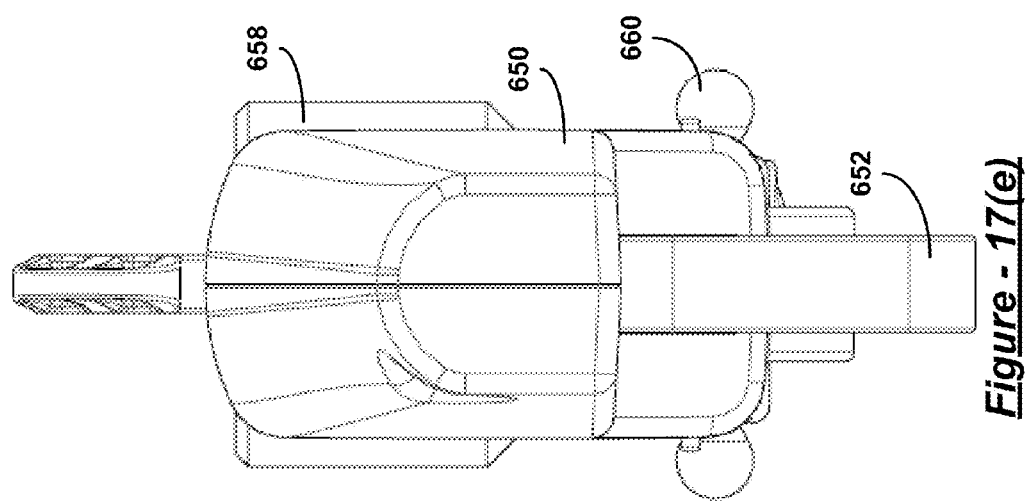

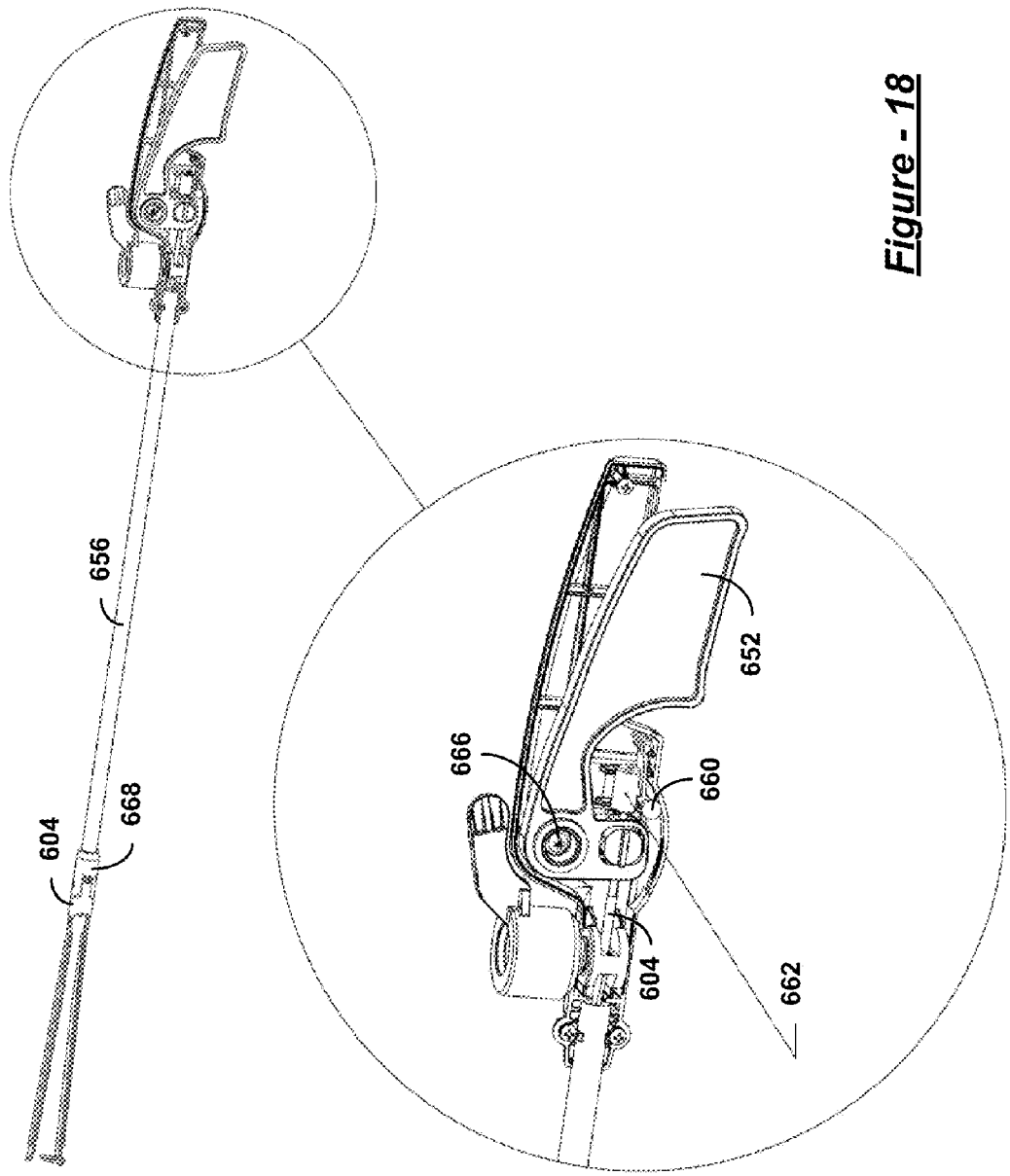

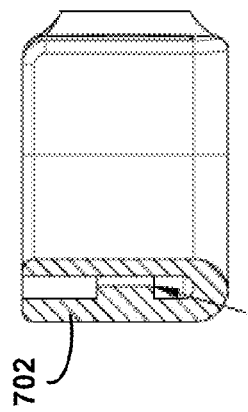
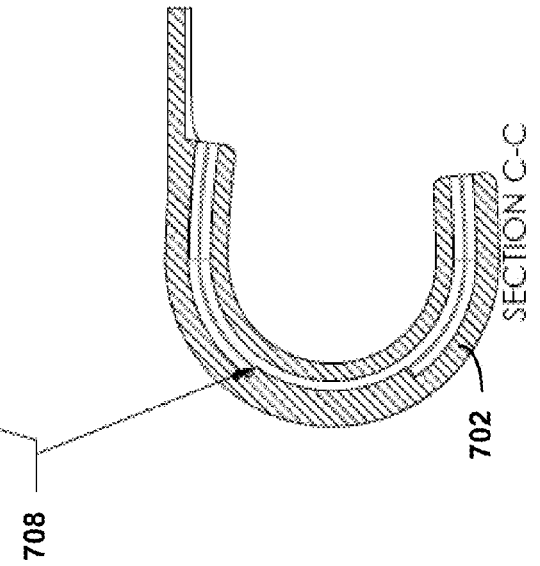
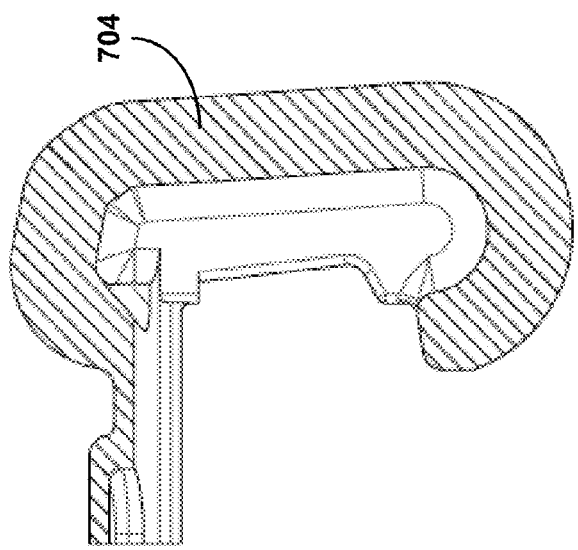

SURGICAL CLAMP AND SURGICAL CLAMP INSTALLATION TOOL

PRIORITY CLAIM

The present application is a non-provisional of U.S. Provisional Patent Application No. 61/299,725 filed Jan. 29, 2010, currently pending, the disclosure of which is hereby incorporated by reference.

FIELD

The present disclosure relates generally to surgical clamps and surgical clamp installation tools.

BACKGROUND

The statements in this section merely provide background information related to the present disclosure and may not constitute prior art.

Recently, there has been increased interest in employing surgical clamps to partition sections of a stomach. An example of a bariatric surgical clamp can be found in Jacobs et al., U.S. patent application Ser. No. 11/984,452 and Jacobs et al., U.S. patent application Ser. No. 11/797,537. The aforementioned patent applications are incorporated by reference herein in their entirety for any purpose.

SUMMARY

In one embodiment, a surgical clamp is configured to operate with an installation tool. The clamp in this embodiment may include two elongated members with a bight portion that joins the two elongated members at a proximal end of the clamp and may bias the two elongated members in an open position at a distal end of the clamp. The bight portion may have one or more engagement features. A clasp mechanism at the distal end of the clamp may include a male component or first component disposed on one of the two elongated members and a female component or second component disposed on the other of the two elongated members at the distal end. The installation tool may include an elongated member with a proximal end and a distal end that has an engagement feature. A handle in this one embodiment may be connected to the proximal end of the installation tool, while a head at the distal end may be configured to receive and/or engage the proximal end of the clamp and may also be operable to articulate in at least one plane.

Further embodiments and apparatuses, including other areas of applicability, will become apparent from the description provided herein. It should be understood that the description and specific examples are intended for purposes of illustration only and are not intended to limit the scope of the present disclosure in any manner.

DRAWINGS

For a more complete understanding of various embodiments of the present invention and the advantages thereof, reference is now made to the following brief description, taken in connection with the accompanying drawings and detailed description, wherein like reference numerals represent like parts, in which:

FIG. 1 is a view of an embodiment of a surgical clamp engaged with an embodiment of a surgical clamp installation tool having an articulating head;

FIG. 2 is a set of views illustrating engagement of the surgical clamp to the articulating head of the surgical clamp installation tool at FIGS. 2(a), 2(b), and 2(c), and actuation of the clamp at FIG. 2(e), to a closed position at FIG. 2(d), and illustrating a six-sided view of the clamp, including a top view at FIG. 2(f), a left side view at FIG. 2(g), a bottom view at FIG. 2(h), a right side view at FIG. 2(i), a view facing the distal end at FIG. 2(j), and a view facing the proximal end at FIG. 2(k);

Figure 5:
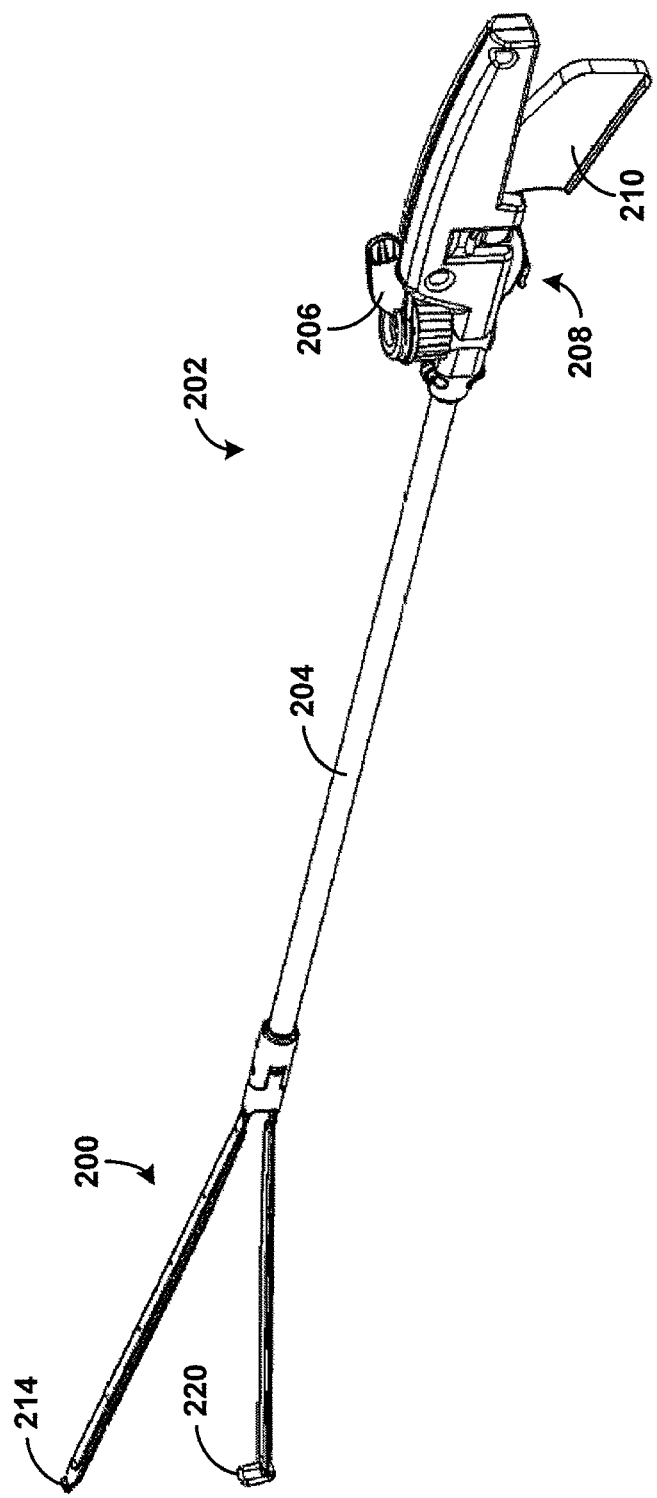
Figure 6A:
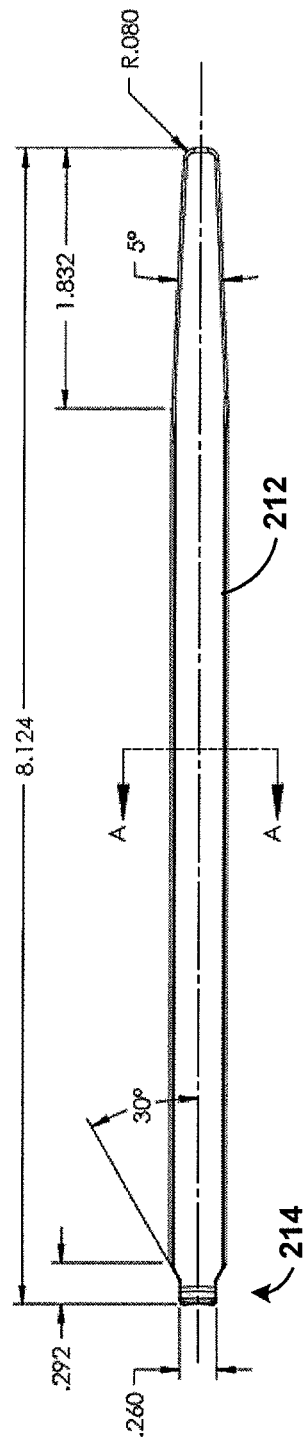
Figure 6B:
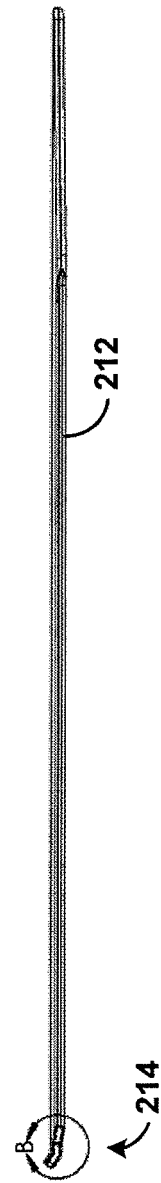
Figure 6D:
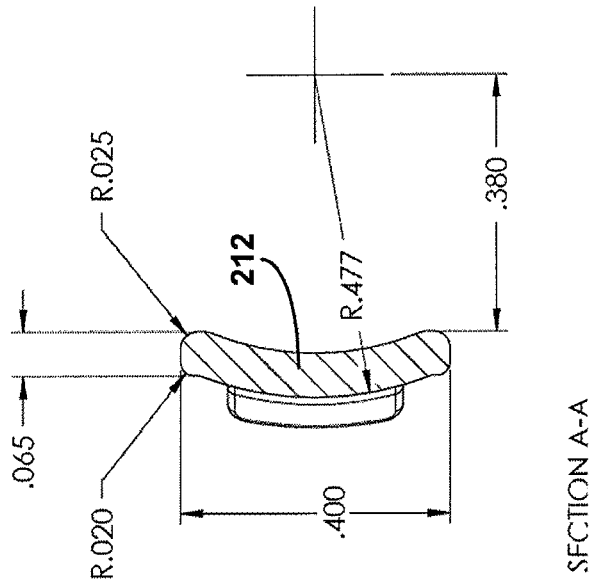
Figure 6C:
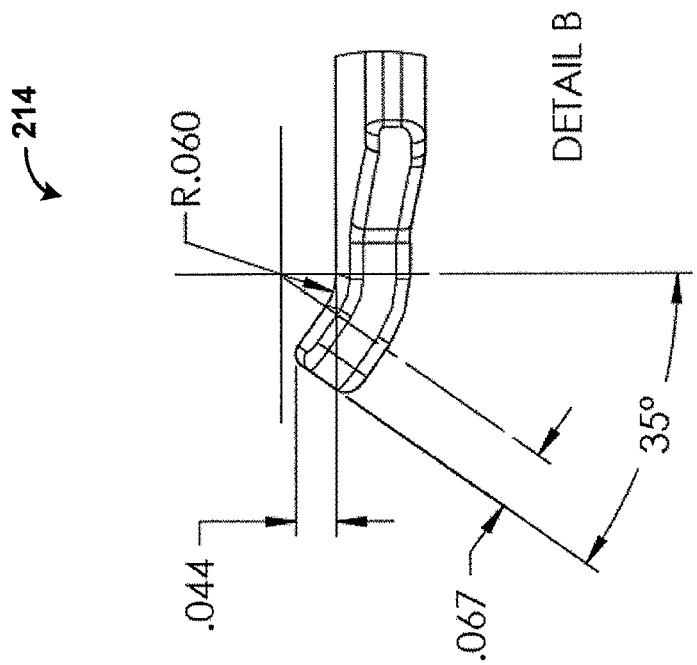

FIGS. 4(b), 4(c), 4(d), and 4(e) provide side cutaway views of various aspects of an embodiment of the surgical clamp installation tool;

FIG. 5 is a view of another embodiment of a surgical clamp engaged with another embodiment of a surgical clamp installation tool having an articulating head;

FIG. 6A is a top view of a rigid member having a male clasp end for the clamp of FIG. 5;

FIG. 6B is a side view of the rigid member of FIG. 6A having the male clasp end for the clamp of FIG. 5;

FIG. 6C is a side view showing the male clasp end of FIG. 6B in greater detail;

FIG. 6D is a cross-sectional view showing a cross-section of the rigid member of FIG. 6A.

Figure 7A:
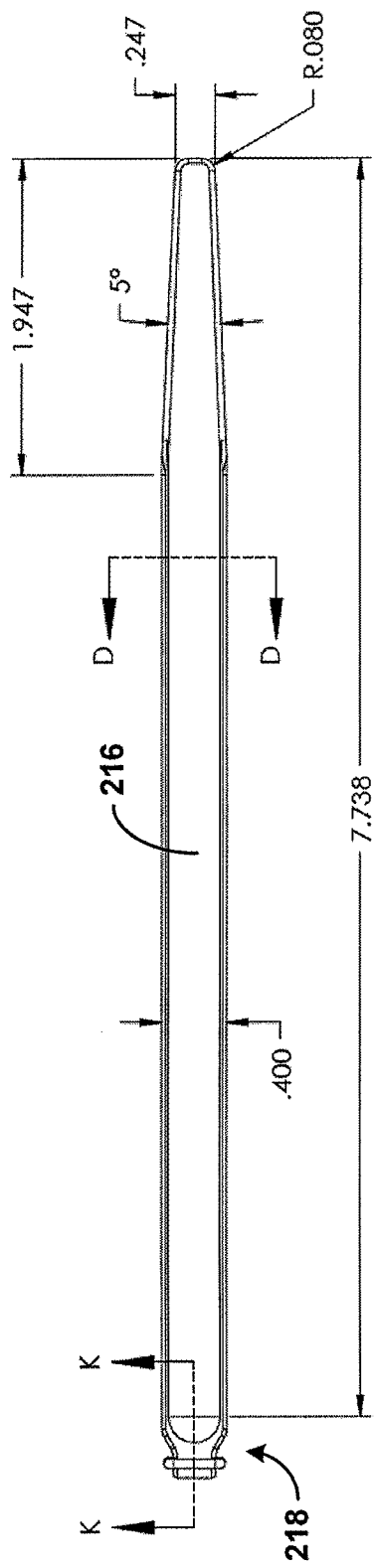
Figure 7B:
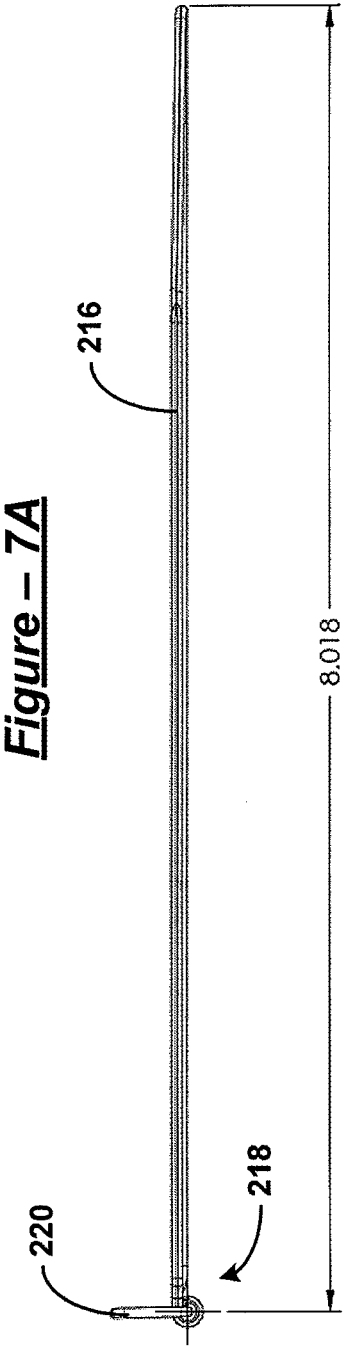

FIG. 7A is a top view of a rigid member having a female clasp end for the clamp of FIG. 5;

FIG. 7B is a side view of the rigid member of FIG. 7A having the female clasp end for the clamp of FIG. 5;

FIG. 7C is a side view showing the female clasp end of FIG. 7B in greater detail;

FIG. 7D is a cross-sectional view showing a cross-section of the rigid member of FIG. 7A.

Figure 8D:
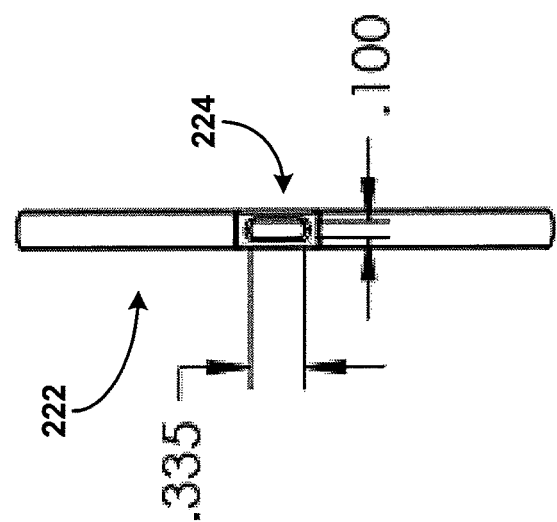
Figure 8C:
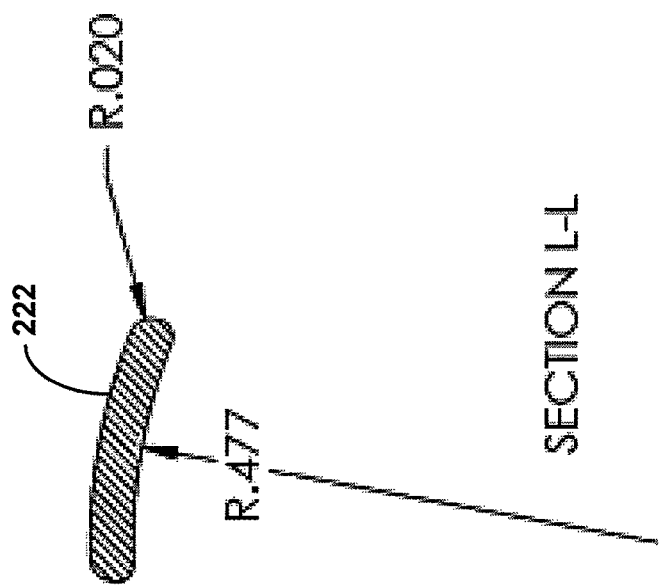
Figure 9D:
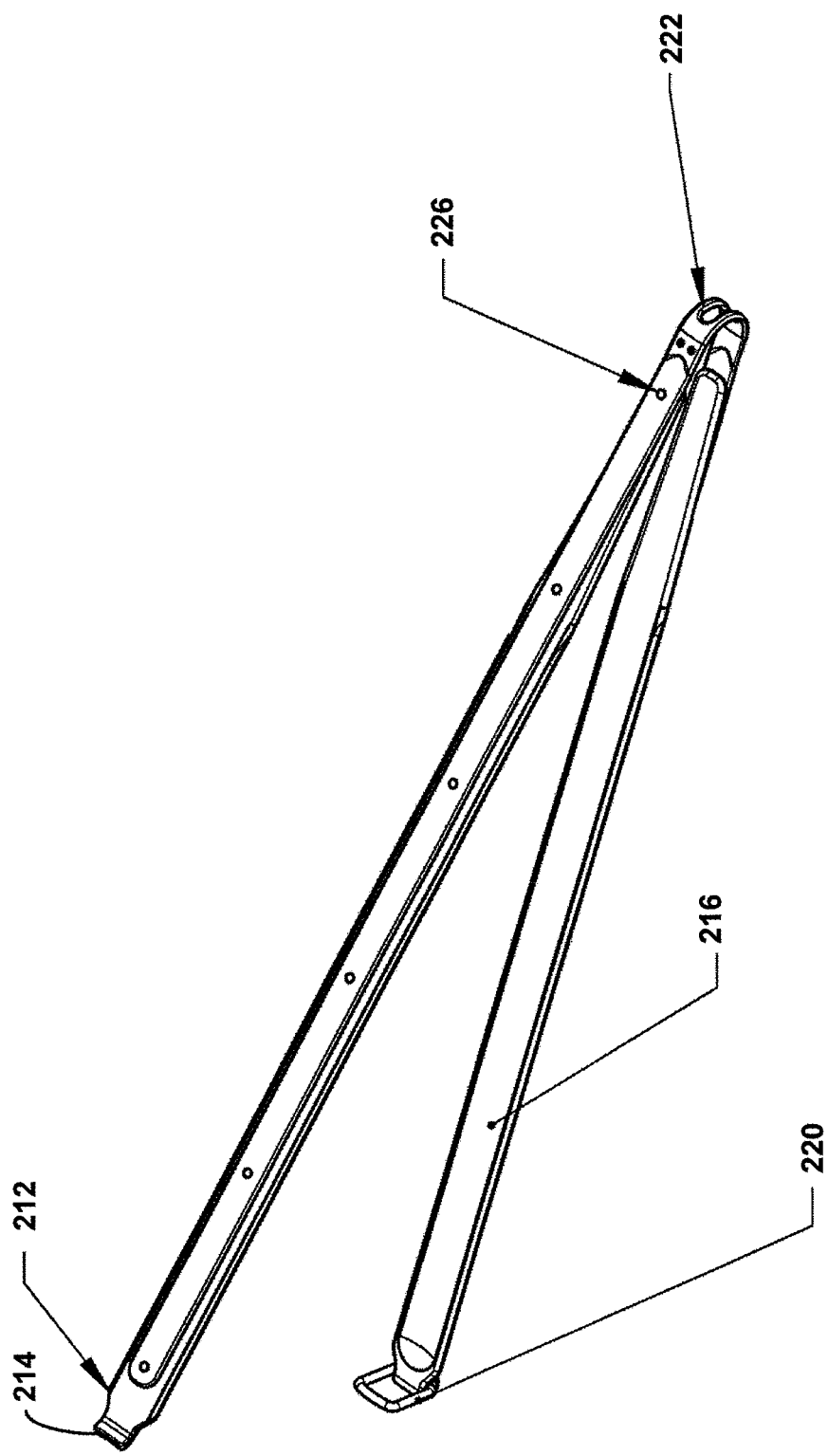
Figure 10:
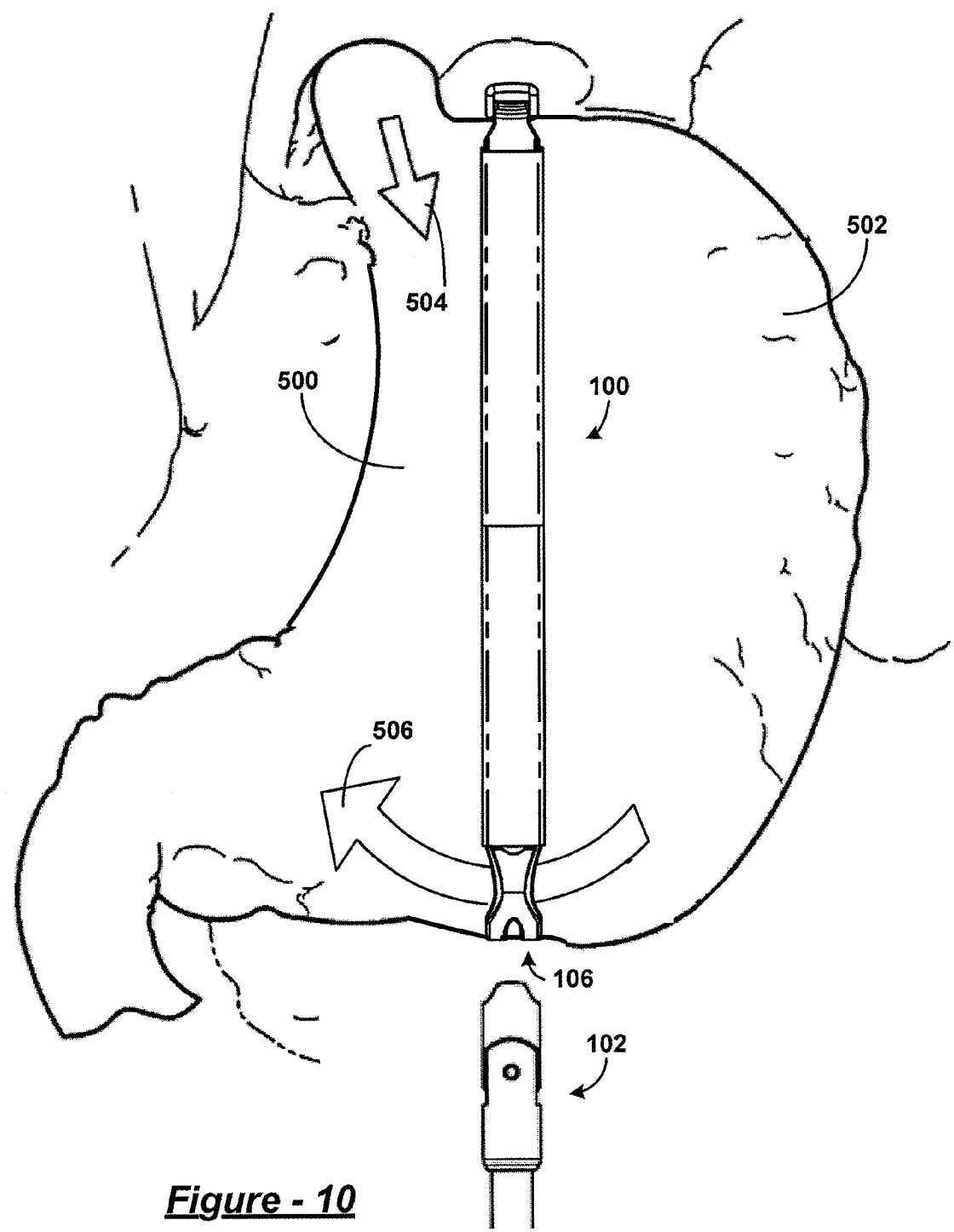
Figure 11:
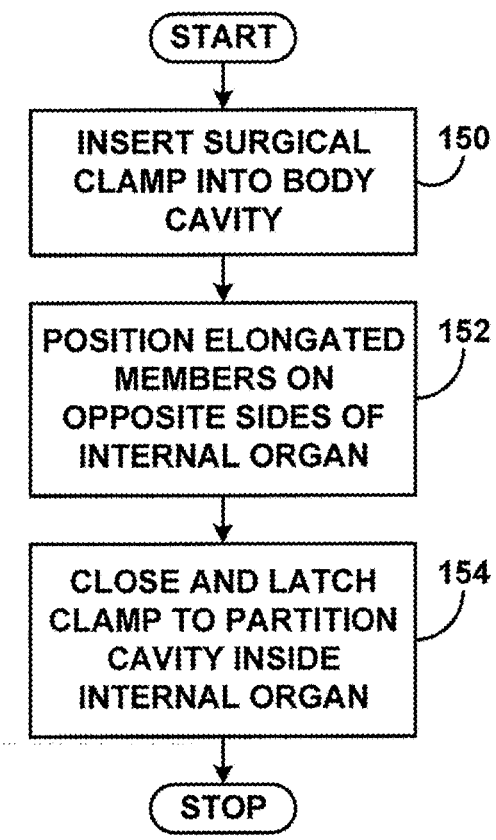
Figure 12:
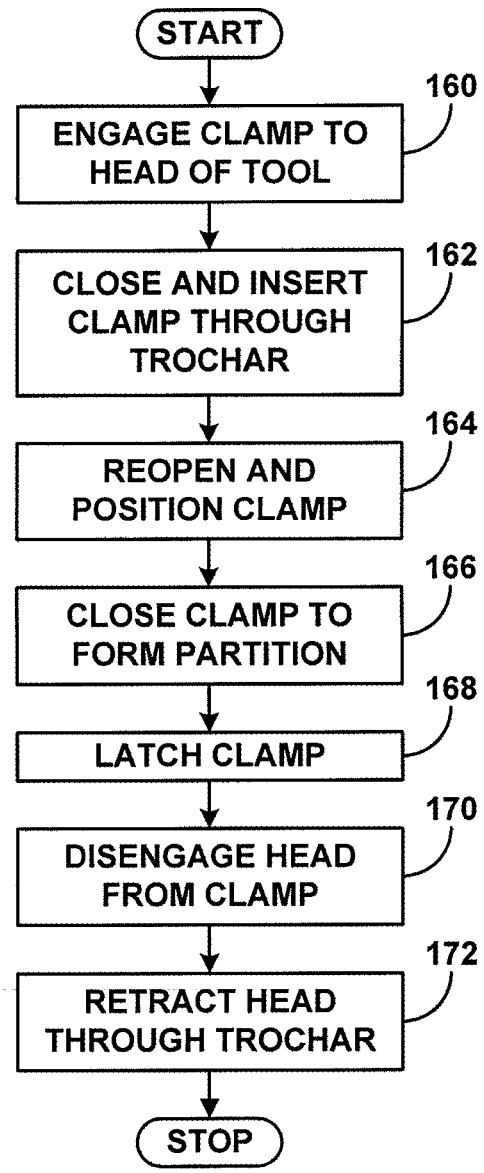

FIG. 8A is a top view of a spring member or the clamp of FIG. 5;

FIG. 8B is a side view of the spring member for the clamp of FIG. 5;

FIG. 8C is a cross-sectional, close-up view showing a cross-section of the spring member of FIG. 8B;

FIG. 8D is a proximal end view of the spring member of FIG. 5;

FIG. 9A is a side view of the clamp of FIG. 5;
FIG. 9B is a bottom view of the clamp of FIG. 5;
FIG. 9C is a proximal end view of the clamp of FIG. 5;
FIG. 9D is a perspective view of the clamp of FIG. 5;
FIG. 10 is a view illustrating the surgical clamp installed in a substantially vertical position on a human stomach;

FIG. 11 is a flow diagram illustrating an embodiment of a method for clamping an internal organ;

FIG. 12 is a flow diagram illustrating another embodiment of a method for clamping an internal organ;

FIG. 13 is a view of yet another embodiment of a surgical clamp engaged with yet another embodiment of a surgical clamp installation tool having an articulating head;

FIG. 14 is a perspective view of the surgical clamp of FIG. 13.

Figure 15A:
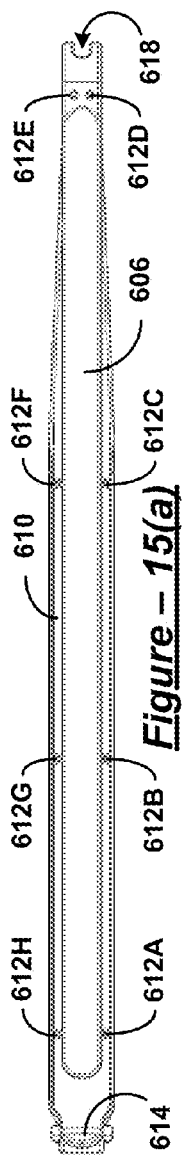
Figure 15B:
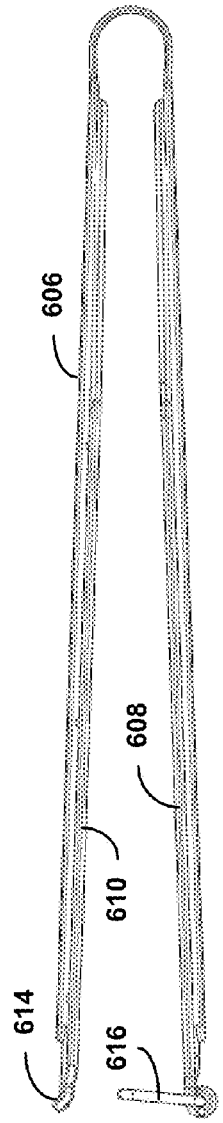
Figure 15C:
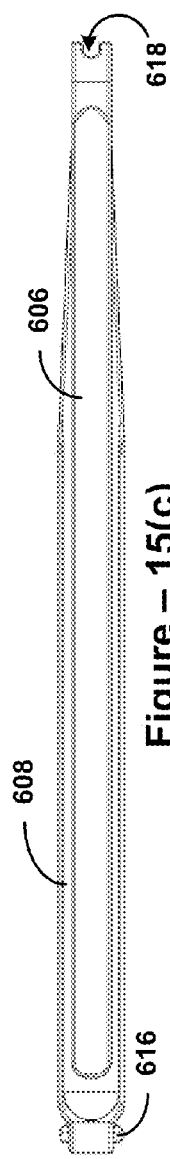

FIG. 15(a) is a top view of the surgical clamp of FIG. 14.
FIG. 15(b) is a left view of the surgical clamp of FIG. 14.
FIG. 15(c) is a bottom view of the surgical clamp of FIG. 14.

Figure 15D:
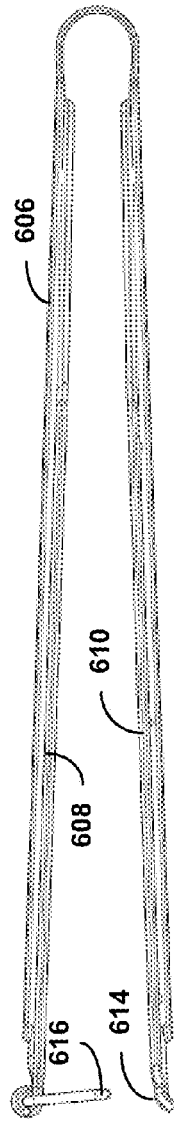

FIG. 15(d) is a right view of the surgical clamp of FIG. 14.

Figure 15F:
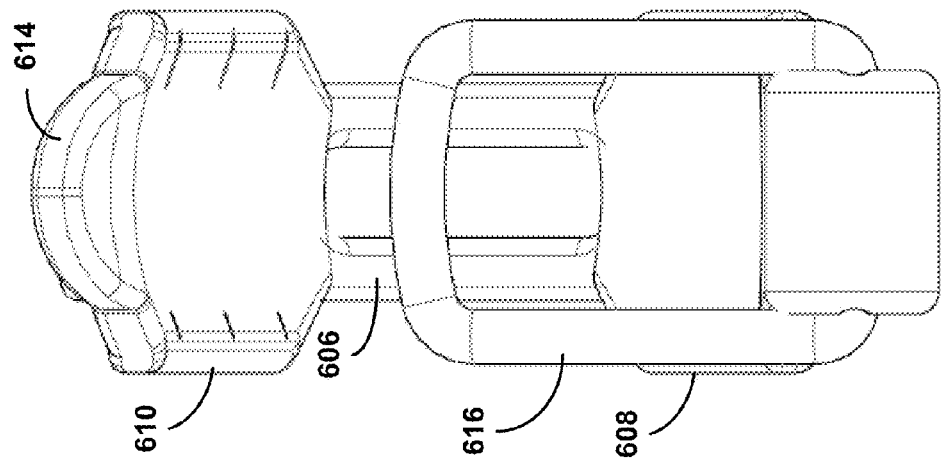
Figure 15E:
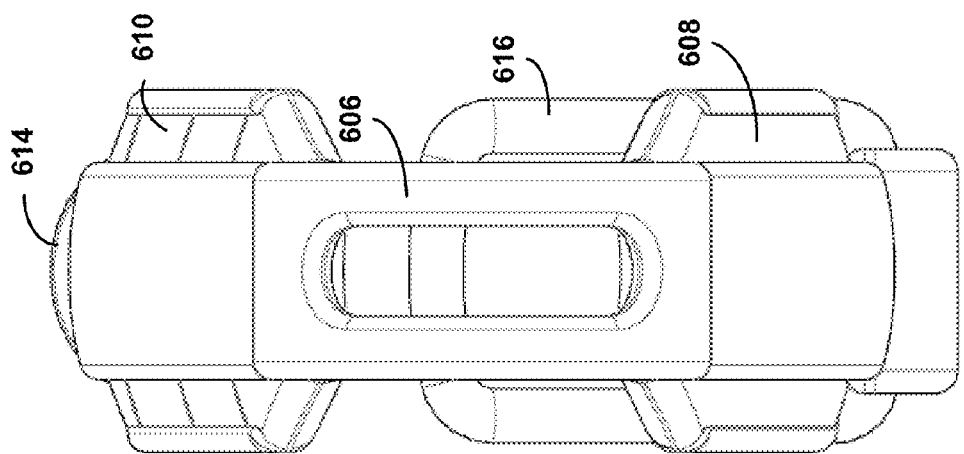

FIG. 15(e) is a proximal spring end on view of the surgical clamp of FIG. 14.

FIG. 15(f) is a distal latch end on view of the surgical clamp of FIG. 14.

Figure 16:
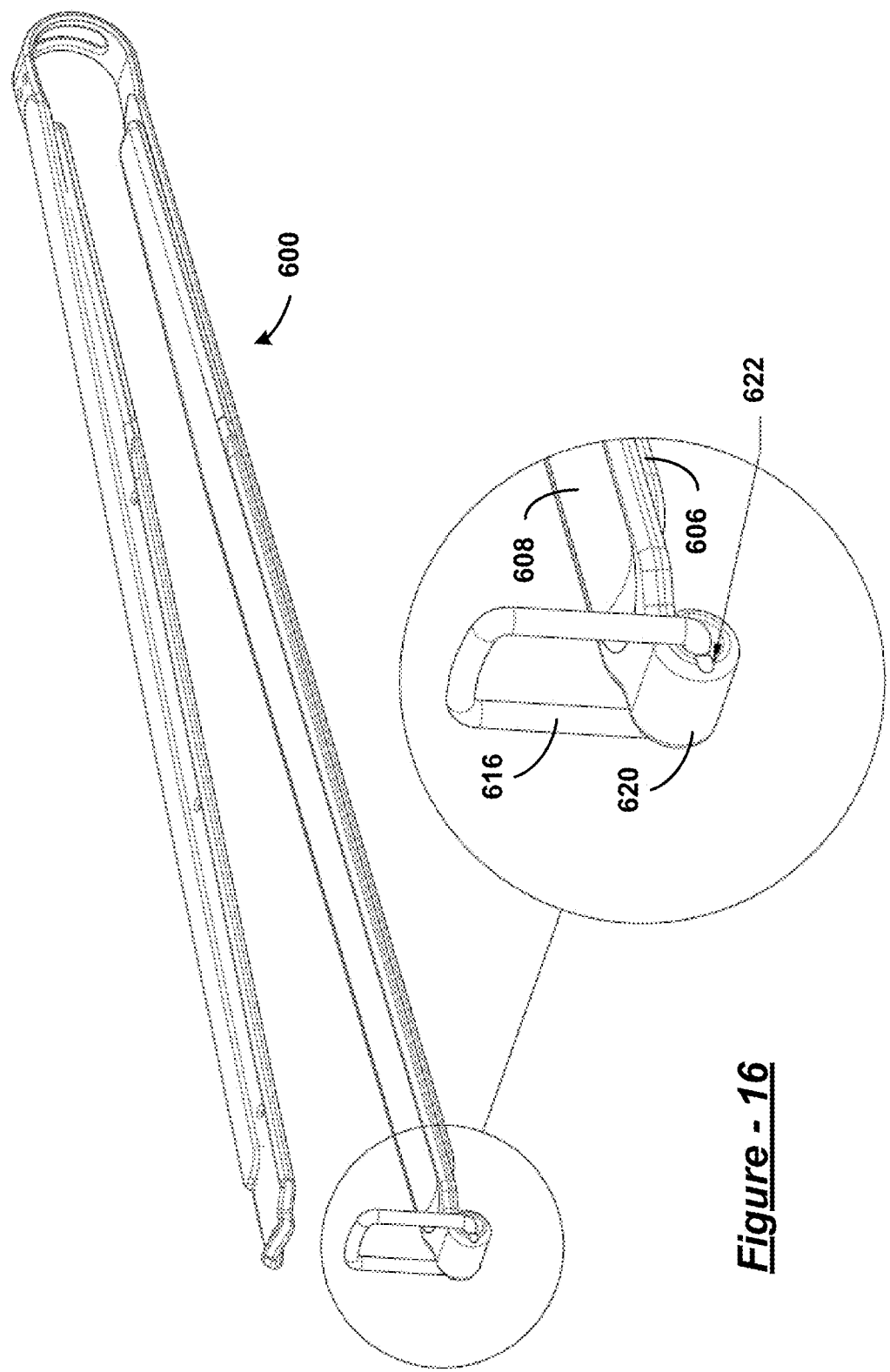

FIG. 16 is a detailed view of a latch end of a bottom arm of the surgical clamp of FIG. 14.

Figure 17A:
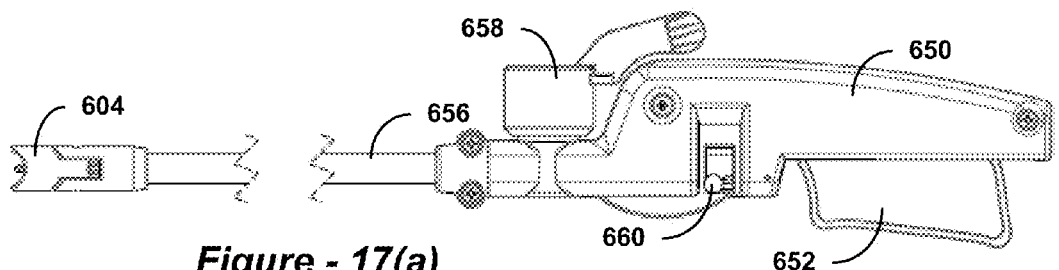

FIG. 17(a) is a top view of the surgical clamp installation tool of FIG. 13.

Figure 17B:
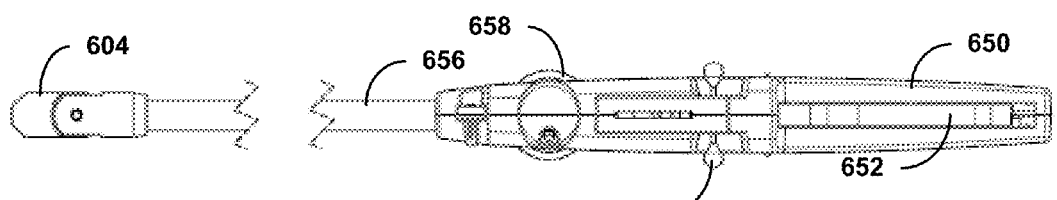

FIG. 17(b) is a left view of the surgical clamp installation tool of FIG. 13.

Figure 17C:
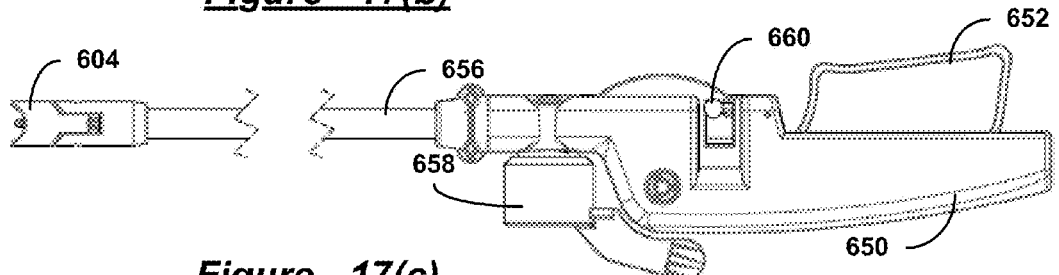

FIG. 17(c) is a bottom view of the surgical clamp installation tool of FIG. 13.

Figure 17D:
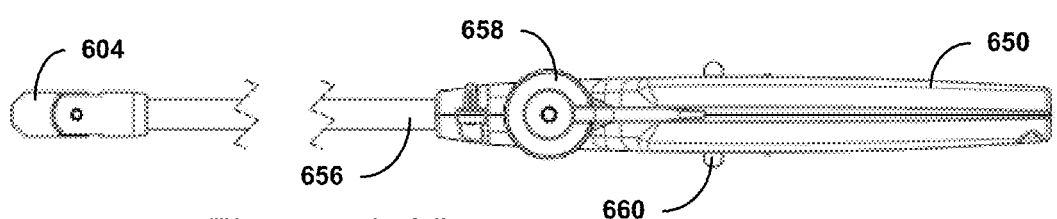

FIG. 17(d) is a right view of the surgical clamp installation tool of FIG. 13.

FIG. 17(e) is a proximal handle end on view of the surgical clamp installation tool of FIG. 13.

FIG. 17(f) is a distal head end on view of the surgical clamp installation tool of FIG. 13.

FIG. 18 is a detailed left side view of a handle end of the surgical clamp installation tool FIG. 13 in which the left side of the handle housing is shown removed.

Figure 19:
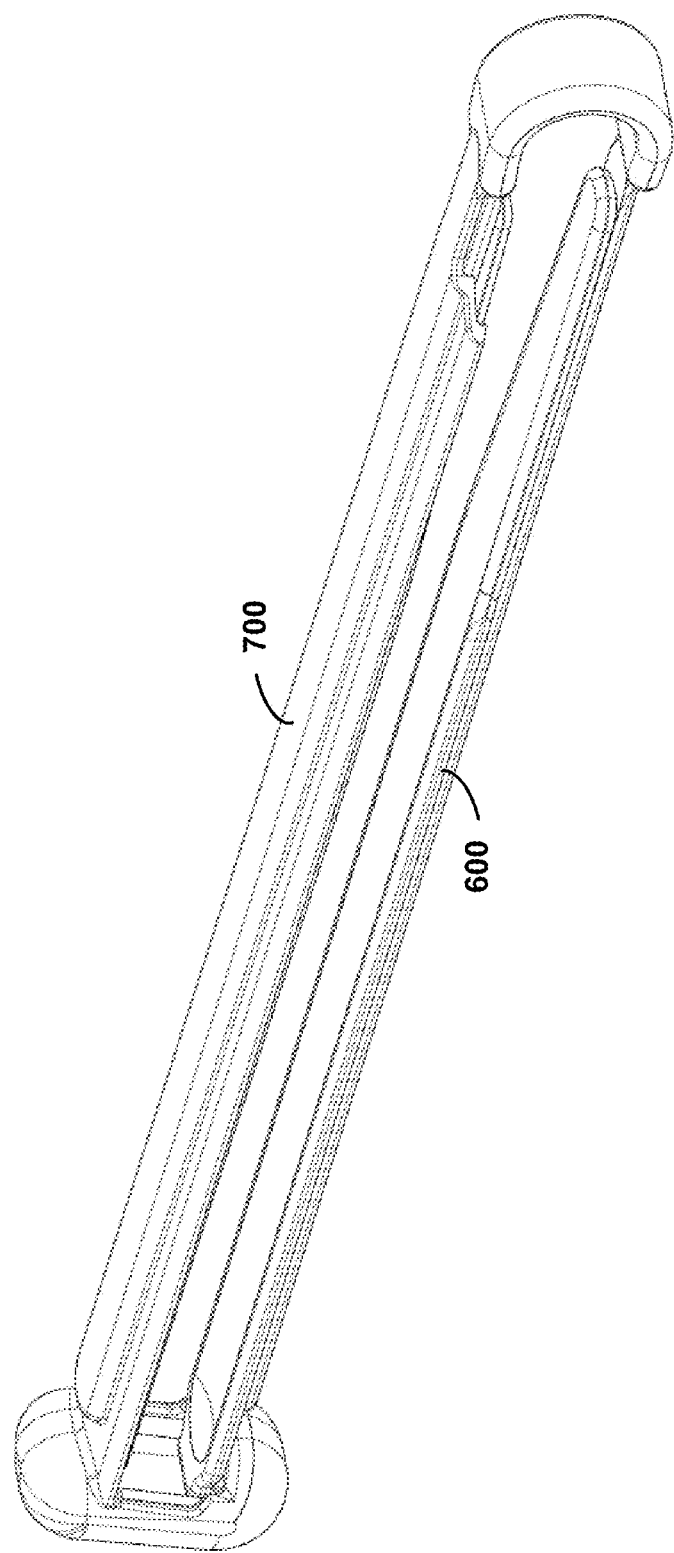

FIG. 19 is a perspective view of the surgical clamp of FIG. 14 having a silicone sleeve engaged therewith.

Figure 20:
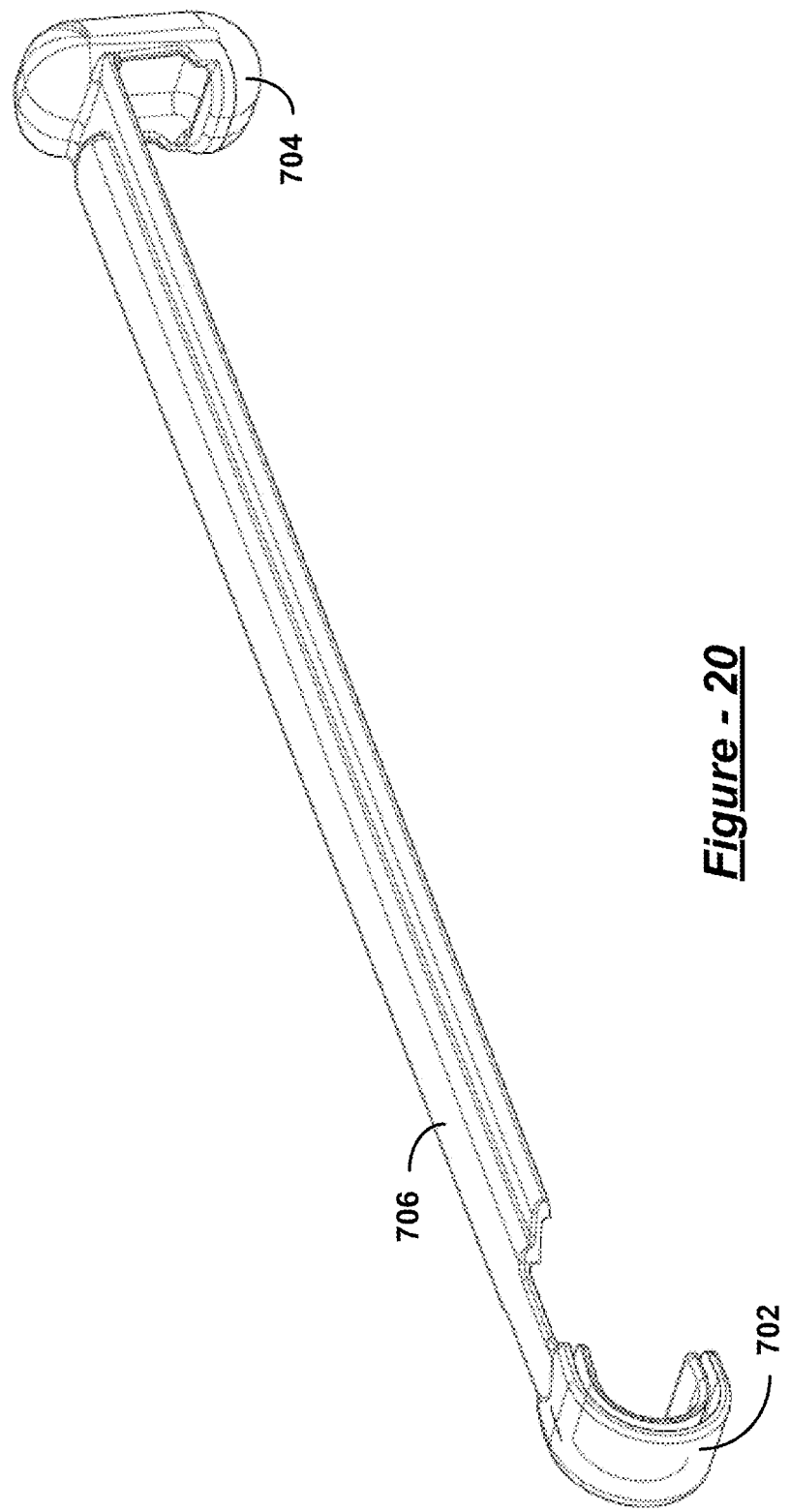

FIG. 20 is a perspective view of the silicone sleeve of FIG. 19 in a disengaged state.

Figure 21:
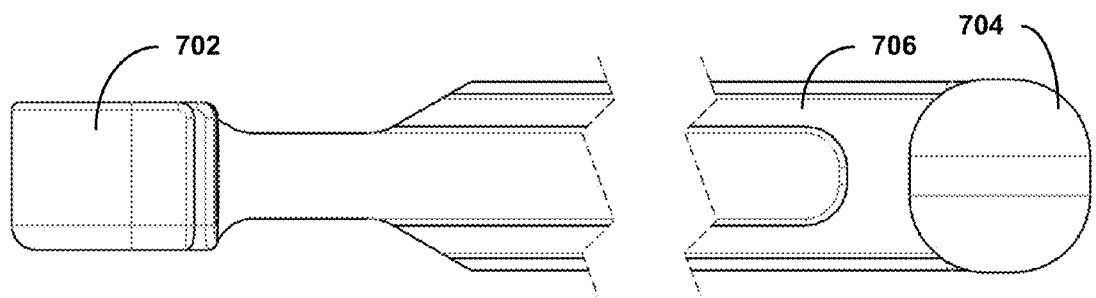

FIG. 21 is a bottom view of the silicone sleeve of FIG. 20.

Figure 22:
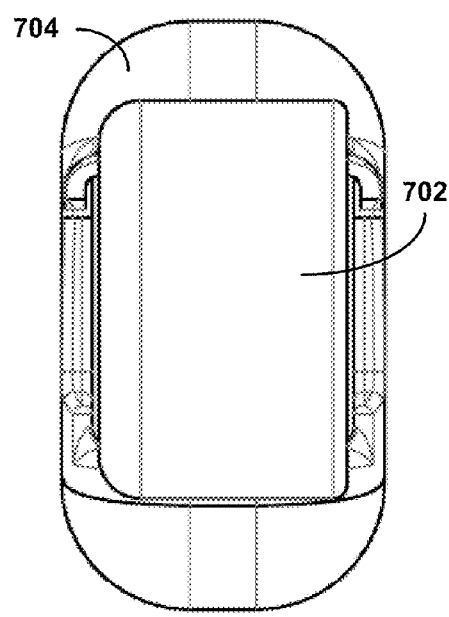

FIG. 22 is a proximal end-on view of the silicone sleeve of FIG. 20.

Figure 23:
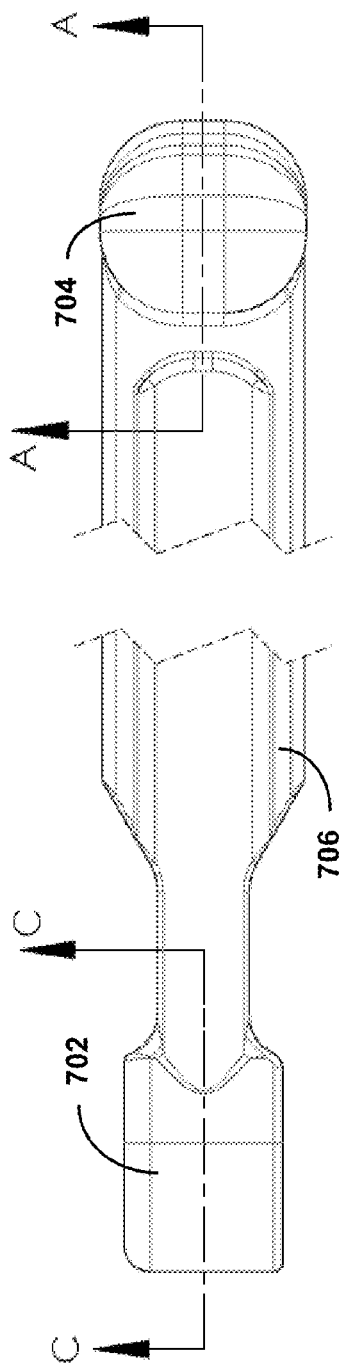

FIG. 23 is a top view of the silicone sleeve of FIG. 20.

Figure 24:
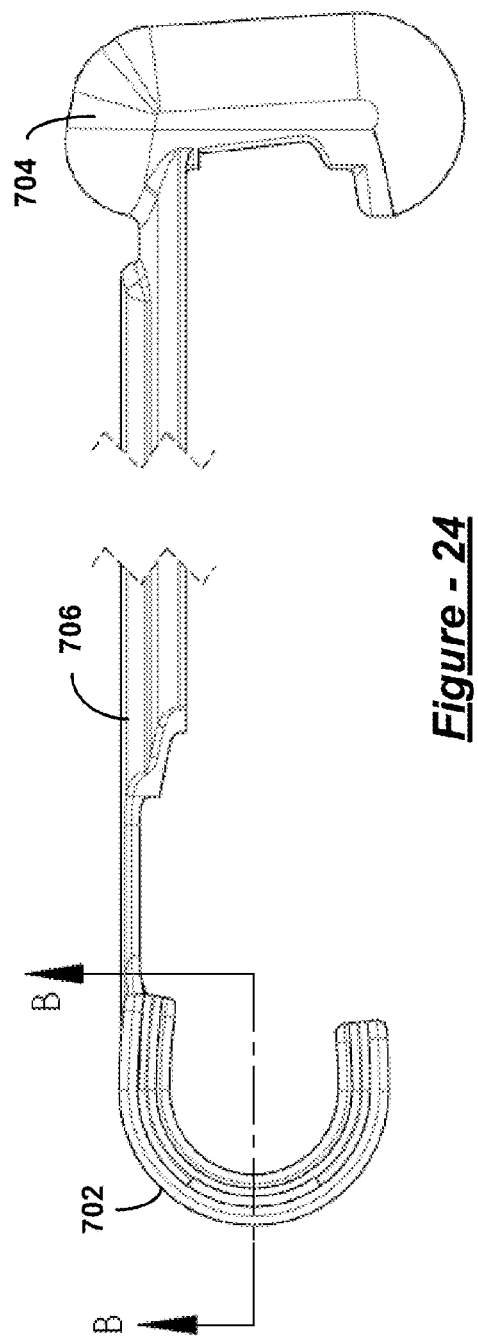

FIG. 24 is a left side view of the silicone sleeve of FIG. 20.

FIG. 25 is a cross-sectional view of a distal end of the silicone sleeve of FIG. 23.

FIG. 26 is a cross-sectional view of a proximal end of the silicone sleeve of FIG. 24.

FIG. 27 is a cross sectional view of a proximal end of FIG. 23.

Figure 28:
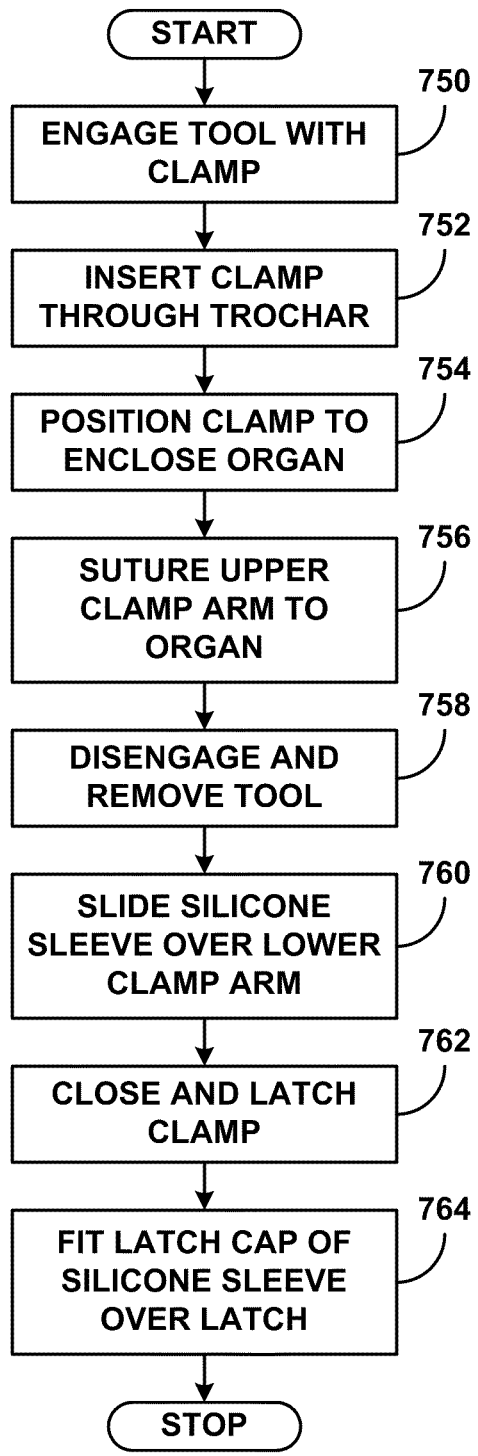

FIG. 28 is a flow diagram illustrating a method of performing endoscopic surgery utilizing the silicone sleeve, clamp, and installation tool of FIGS. 13-27.

For FIGS. 5-9, dimensions are given in inches. However, it should be understood that various embodiments are not limited to the dimensions provided. Such dimensions are purely illustrative.

For FIGS. 4(b), 4(c), 17(a)-17(d), 21, 23, and 24, broken lines indicate variability in length of the discontinuous portions.

DETAILED DESCRIPTION

The following description is merely exemplary in nature and is not intended to limit the present disclosure, application, or uses. It should be understood at the outset that although an exemplary implementation of the present invention is illustrated below, the present invention may be implemented using any number of techniques, whether currently known or in existence. The present invention should in no way be limited to the exemplary implementations, drawings, and techniques illustrated below, including the exemplary design and implementations illustrated and described herein. Additionally, the drawings contained herein are not necessarily drawn to scale, and may be provided in a variety of different dimensions, shapes and configurations. Any provided dimensions are provided only to illustrate a particular exemplary implementation, and in no way construed to limit the present invention absent an explicit recitation of such dimensions and then only with respect to the claim or claims reciting the dimension or dimensions.

Figure 1:
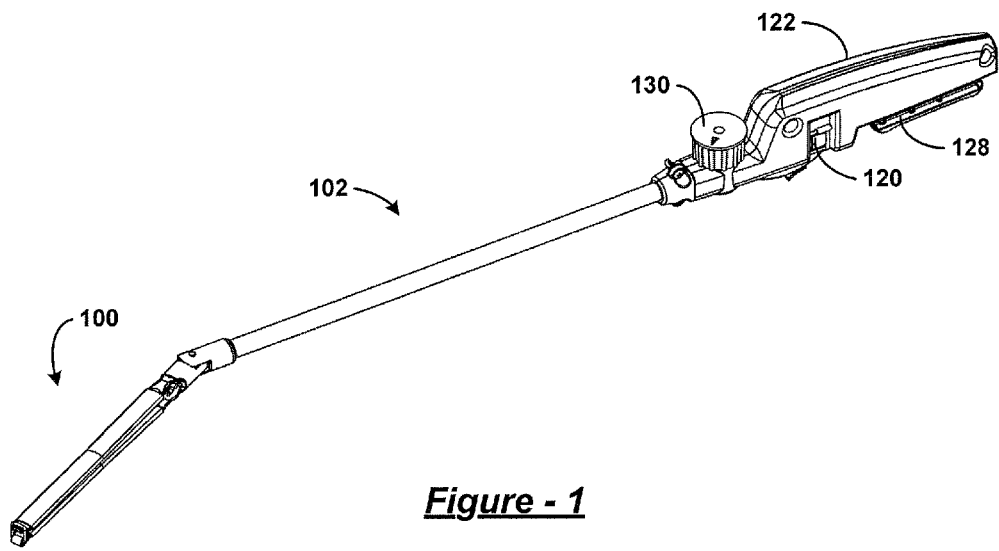

Referring to FIG. 1, an embodiment of a surgical clamp 100 engages with an embodiment of a surgical clamp installation tool 102. In these embodiments, the clamp 100 and the installation tool 102 are designed for performing bariatric surgery through a surgical trochar. The clamp 100, in a preferred embodiment, may be approximately fifteen to thirty centimeters in length to accommodate partitioning of a human stomach. To accommodate insertion through a trochar, the closed clamp 100 will preferably have a diameter or circumference less than fifteen millimeters over the entirety of its length or along the majority of its length. A non-handle section of the installation tool 102 intended for insertion through the trochar has a similar diameter or a smaller diameter. It is envisioned that other embodiments of the clamp and installation tool can be of other sizes. It is additionally envisioned that the clamp may be articulated in at least one plane to provide different angles and lengths of partition to the stomach. It is also envisioned that other embodiments of the clamp and installation tool can be for clamping other parts of the human body and/or for clamping other types of bodies or structures.

Referring to FIG. 2, the surgical clamp 100 has two elongated members 104A and 104B. A bight portion 106 joins the two elongated members at a proximal end of the clamp 100 and biases the two elongated members in an open position at a distal end of the clamp 100. As used herein, a bight is a loop, bend, hinge, corner angle, hollow, fold, or similar structure. The bight portion has one or more engagement features, such as, for example, a slotted aperture 108 such as that shown in FIG. 2(b). A clasp mechanism, in one embodiment, has a male component 110 disposed on one of the two elongated members at the distal end, and a female component 112 disposed on the other of the two elongated members at the distal end.

Figure 2A:
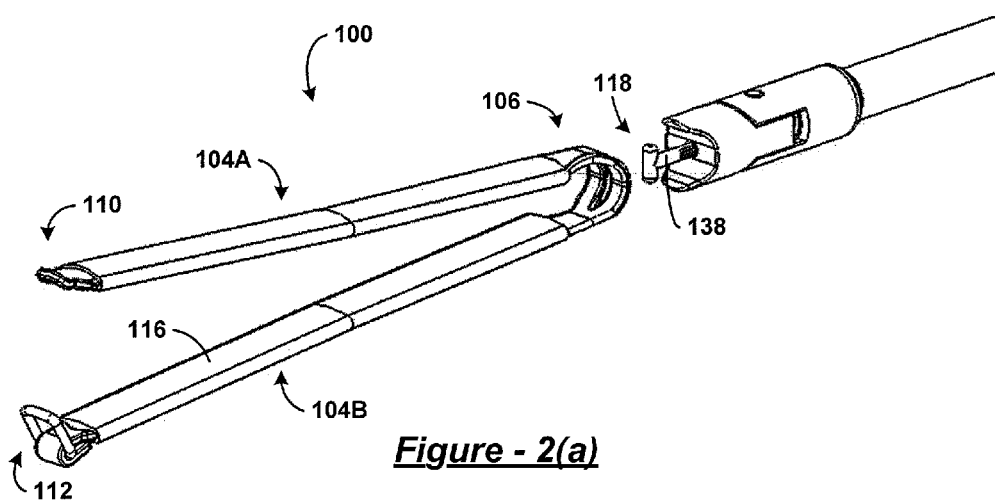

Particularly to partially partition a stomach in performing bariatric surgery, spacing between the two elongated members 104A and 104B effects two or more clamp sections as best shown in FIG. 2(e). At least one of the sections is a partition forming section 105A located nearer the distal end of the clamp 100 than the proximal end of the clamp 100. At least another of the sections is a passage forming section 105B located nearer the proximal end of the clamp 100, such as near the bight portion 106, than the distal end of the clamp 100.

In order to reduce injury to the partitioned organ, a padding material 116 can be connected to one or more of the two elongated members. For example, padding material 116 can connect to the elongated member 104B at least at a location corresponding to at least part of the partition forming section. In some embodiments, the padding material can be composed predominantly of silicone or fully of silicone. It is also envisioned that the opposing limbs of the clamp may be fitted with magnets to facilitate closure.

Figure 2B:
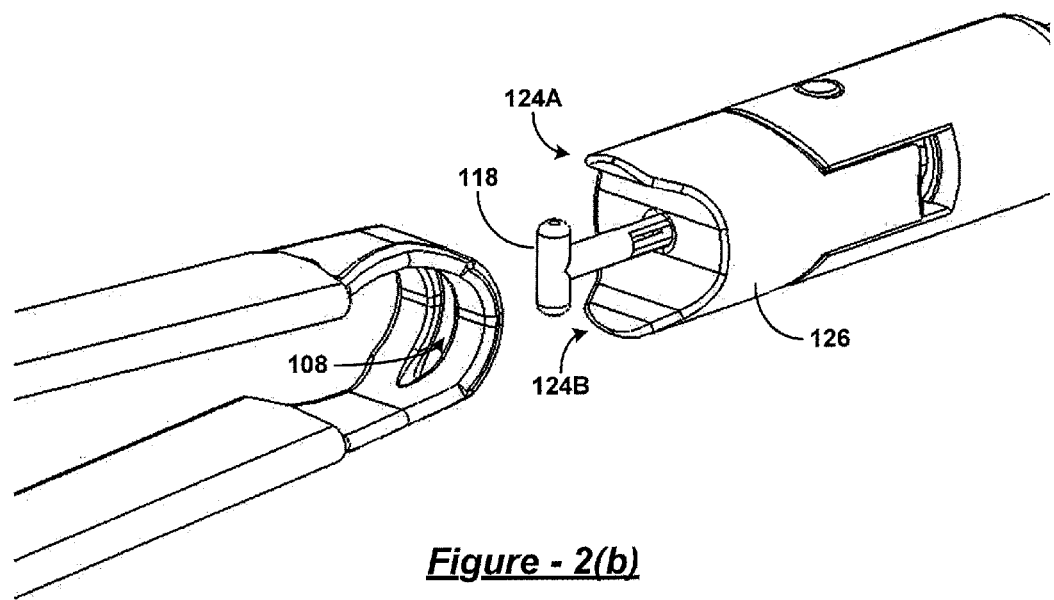
Figure 2C:
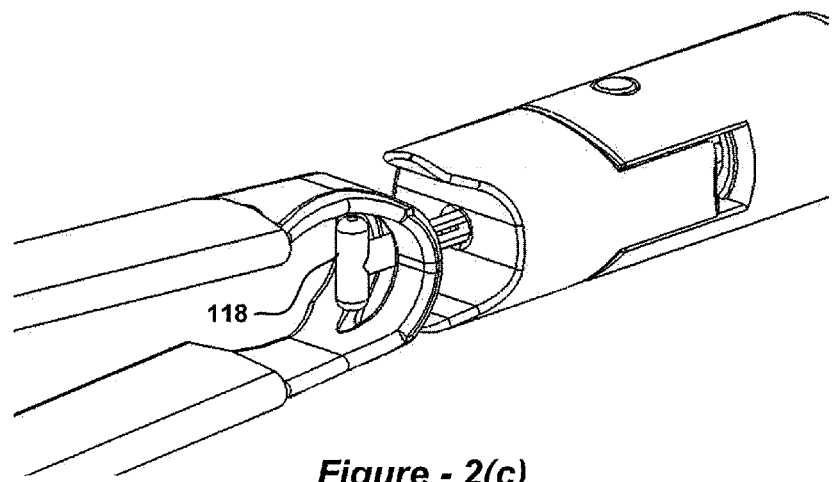
Figure 2F:
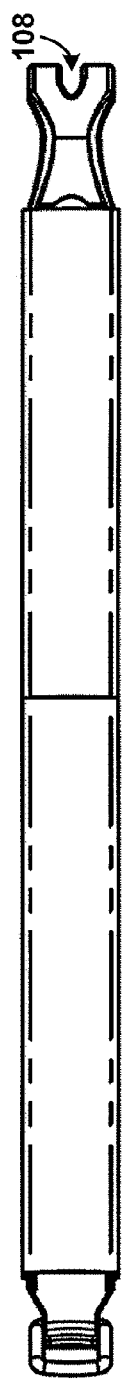
Figure 2G:
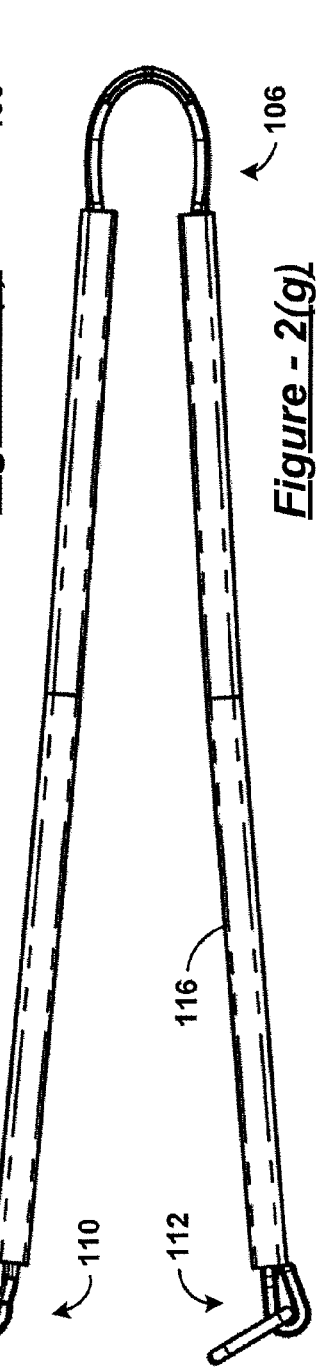
Figure 2H:
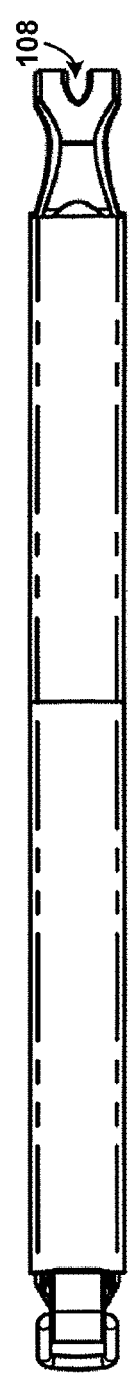
Figure 2I:
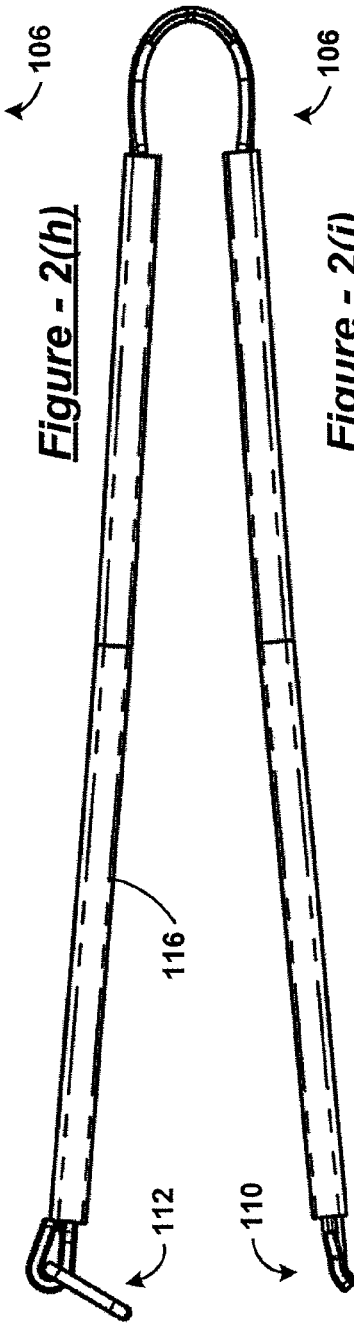
Figure 2K:
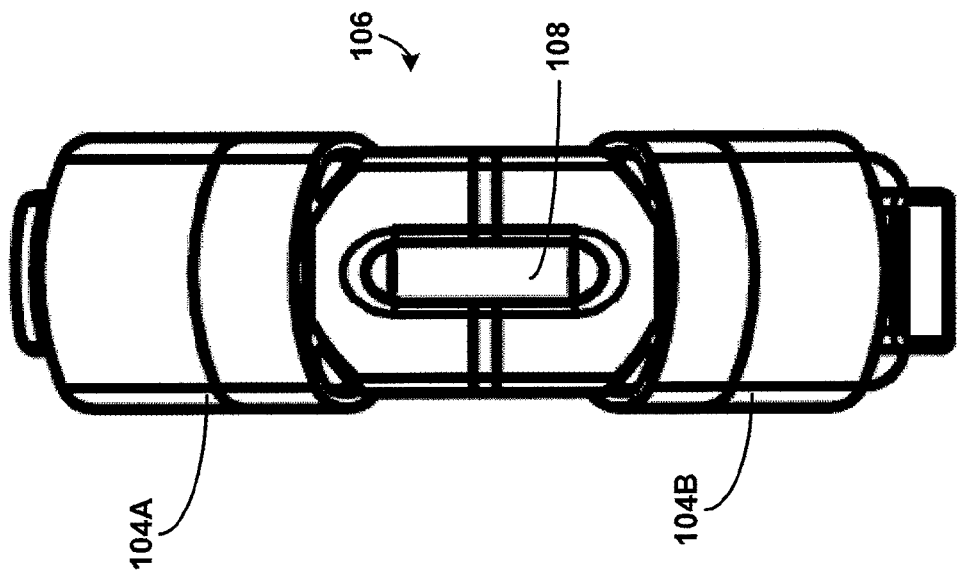
Figure 2J:
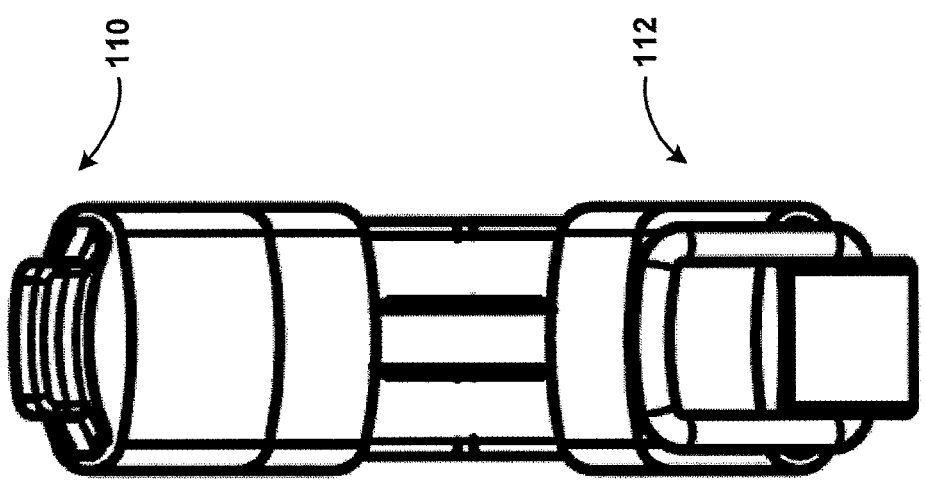
Figure 3A:
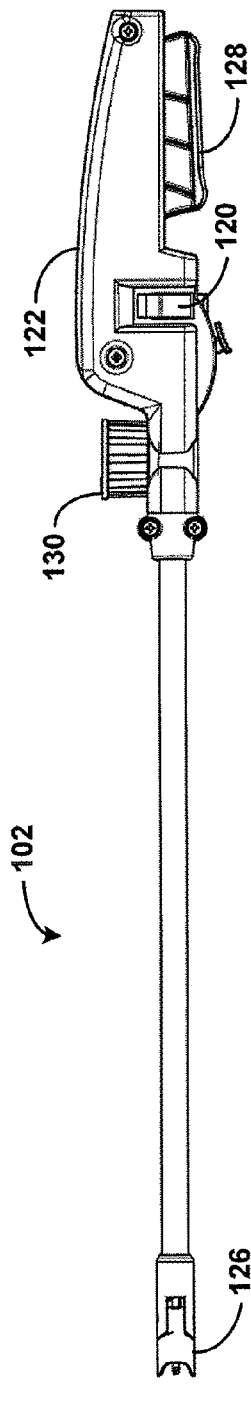
FIG. 3 is a set of views illustrating the surgical clamp installation tool from six sides with the right side of the housing of the handle shown removed, including a left side view at FIG. 3(a), a top view at FIG. 3(b), a right side view at FIG. 3(c), a bottom view at FIG. 3(d), a view facing the distal end at FIG. 3(e), and a view facing the proximal end at FIG. 3(f)
Figure 3B:
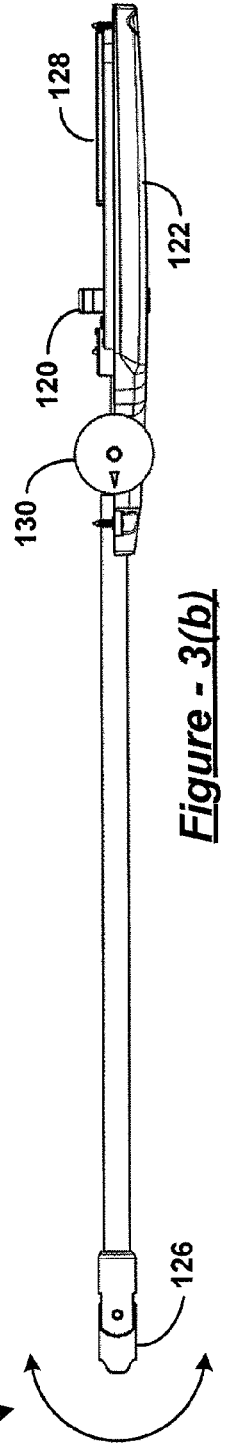
Figure 3C:
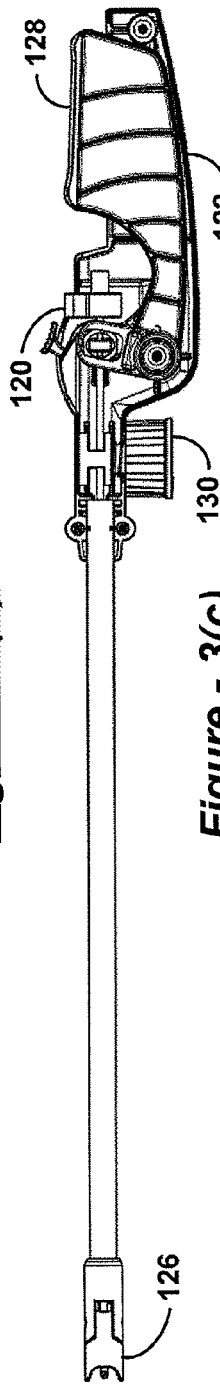
Figure 3D:
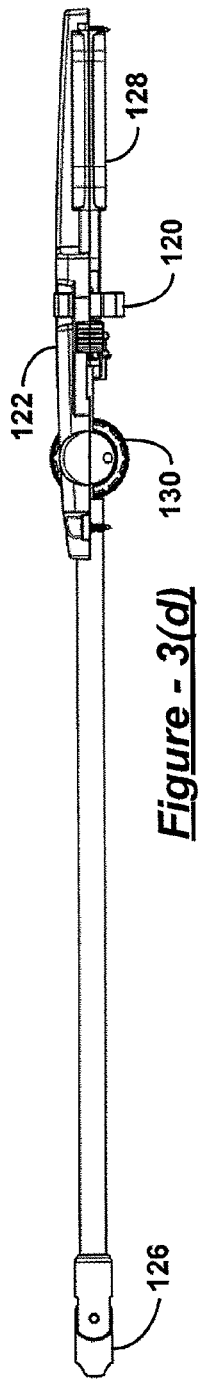

In some embodiments, the engagement feature at the proximal end of the clamp 100 can be a slotted aperture 108 as shown in FIG. 2(b) having a width and a length larger in size than the width. The length of the slotted aperture can be oriented perpendicular or angled with reference to a longitudinal axis of the clamp 100. It is envisioned that other types engagement features can be employed, such as a socket, a loop, a hook, a clasp, a string, magnetic, etc.

In some embodiments, the male component 110 of the clasp at the distal end of the clamp can be an end of the elongated member 104A that flares away from a longitudinal axis of the clamp when the clamp is forced to a closed position. Accordingly, the female component 112 can be a loop attached to the end of the elongated member 104B and disposed to engage the male component 110 of the elongated member 104A when the clamp is forced to the closed position. This can be seen more clearly in connection with FIG. 2(e). It is envisioned that other types of clasp components can be employed, such as those found in a hinge, such as a living hinge, hook and loop, spring ring, lobster or trigger, toggle, tube, bolt and bolt hole, screw and threaded aperture, or any other type of closure arrangement.

Returning to FIG. 1 and referring generally to both FIG. 1 and FIG. 2, the clamp 100, in use, engages with the installation tool by the slotted aperture 108. For example, the installation tool 102 has an elongated member, such as a pull-rod 138, having a proximal end and a distal end that has an engagement feature. The distal end of the elongated member of the installation tool 102 engages with the proximal end of the clamp 100 through the slotted aperture 108 of the bight portion 106. In some embodiments, the engagement feature takes the form of a T-bar 118. This T-bar 118 is sized and shaped to allow insertion thereof through the slotted aperture 108 to engage the clamp 100. It is envisioned that another engagement feature may have an X-shape, and be sized for insertion through an X-shaped slot in the clamp. Other shapes are also possible.

The installation tool 102 may include a lever radially engaged with the pull-rod at its proximal end at a handle 122 that may be configured as a thumbwheel 120 that extends out of the handle 122 of the installation tool 102 through an aperture. While the T-bar 118 is inserted through the slotted aperture 108, actuating the thumbwheel 120 can cause the T-bar 118 to rotate ninety degrees as illustrated in one embodiment from a first position shown in FIG. 2(c) and in a second position as shown in FIG. 2(d).

At this point, retracting the pull rod, which may be achieved by squeezing a trigger 128 to retract the pull rod, forces the proximal end of the clamp 100 up against and progressively further between guide members of the surgical clamp installation tool 102, such as a pair of wedges 124A and 124B, formed in the articulating head of the installation tool 102. A curvature or incline imparted to the articulating head of the installation tool 102 by the pair of wedges can be keyed to a curvature or incline of the bight portion 106 of the clamp 100 in such a way that fully or more fully retracting the pull-rod forces the normally open clamp 100 to a closed position such as that shown in FIG. 2(e).

Turning to FIGS. 2(f)-2(k), the various clamp features can be readily appreciated. These features include bight portion 106, slotted aperture 108, male component 110, female component 112, and padding material 116. It should be readily understood that the padding material 116 can be configured as a pair sleeves as shown, but that other configurations may also be employed. Moreover, non-linear shapes may be utilized for various types of applications in clamping various types of organs, as desired.

Turning now to FIG. 3 and referring generally to FIG. 1 and FIG. 3, retraction of the pull-rod of the installation tool 102 is accomplished by actuation or movement of another lever or trigger that is engaged to the proximal end of the pull-rod, such as through an axial engagement. This lever can be configured as the trigger 128 that extends out of the handle 122 through an aperture or slotted opening. The shape of the handle and disposition of the trigger are, preferably, ergonomically configured to allow the surgeon to hold the installation tool parallel to the ground near waist level to grip the handle 122 and the trigger 128 in one hand. The thumbwheel 120 is disposed to be within easy reach of the thumb of that hand to facilitate holding of the clamp 100 by the surgeon in the other hand while engaging the clamp to the articulating head 126. The thumbwheel 120 may be conveniently adjusted to rotate the T-bar 118 to a desired position to lock the T-bar 118 to the clamp 100 at the bight portion 106 through the slotted aperture 108. In one embodiment, the thumbwheel 120 may rotate the T-bar 118 by ninety degrees.

Once the surgeon has rotated and retracted the pull-rod using T-bar 118 and trigger 128 with one hand, the surgeon's other hand becomes free for other tasks, such as actuating yet another lever protruding from the handle 122 and configured, for example, as a dial 130. With the clamp 100 pulled closed or partially closed against the pair of wedges, the head 126 can be articulated from side to side by rotating this dial 130. The motion of the articulating head 126 through rotation of the dial 130 is illustrated in one embodiment in the top view of the installation tool 102 in FIG. 3(b) at arrow 300 showing a range of motion or articulation in one embodiment.

Figure 4A:
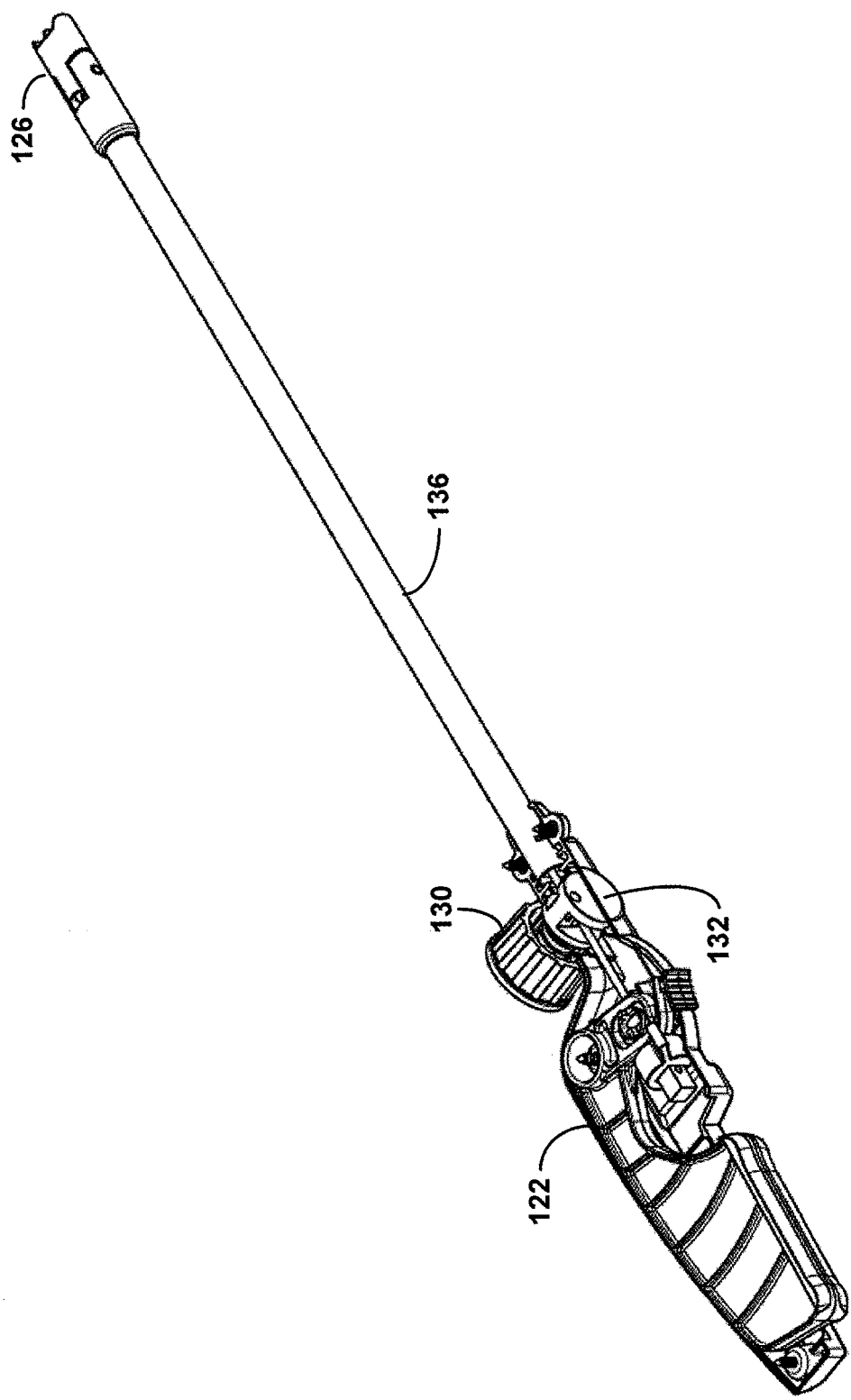
FIG. 4(a) is a perspective view illustrating an exemplary surgical clamp installation tool with the right side of the housing of the handle shown removed.

Turning now to FIG. 4, in some embodiments, turning the dial 130 can turn a hub 132 or connector inside or adjacent the handle 122 that is connected to a pair of guidelines 134A and 134B. These guidelines 134A and 134B, together with pull-rod 138, may extend through an elongated, rigid sleeve, such as a cylindrical tube 136, for connection on either side of a swivel mount of the articulating head 126. It is envisioned that the guidelines can be flexible or rigid, that the cylindrical tube 136 can be rigid or semi-rigid, and that the pull-rod 138 can be rigid or semi-rigid. By semi-rigid, it is meant that the pull-rod 138 can be flexible or partially flexible at least in the plane of articulation along at least part of its length near the distal end of the installation tool 102, but still axially and rotationally rigid or semi-rigid along its length. Thus, when the installation tool 102 and clamp 100 are held parallel to the ground, the pull-rod 138 can be rotated and retracted by actuation of the thumbwheel 120 and trigger 128, and the head 126 can be articulated in a plane orthogonal to the gravity vector by manipulation of the dial 130. The plane of articulation may be adjustable in certain embodiments, or may be set in a desired plane that is not orthogonal to the gravity vector.

Turning now to FIG. 5, other embodiments of the clamp 200 and installation tool 202 can include a clamp 200 made of multiple pieces, a longer main tube 204, and a thumb lever 206 on the dial 130 to articulate the head of the tool 102 that is attached to the clamp 200. In some embodiments, the clamp 200 can be a three-piece clamp. A ratchet release 208 can also be provided on the installation tool 202 that, when pressed, allows the pull rod to extend, which in turn will release the clamp 200 allowing it to reopen. In other words, as the surgeon presses on the trigger 210, causing the pull-rod to retract and the clamp 200 to close, a ratchet mechanism catches the trigger 210 in the pressed in position. Thus, the pull-rod will remain retracted and clamp 200 will not reopen even if the surgeon releases pressure on the trigger 210.

Turning now to FIG. 6, and referring generally to FIGS. 6A-6D, one piece of a three-piece clamp can be a rigid member 212 having a male clasp end 214. As will be described further below with reference to FIG. 9, this rigid member 212 serves as one of the elongated members of the clamp 200 for forming the partition that divides the stomach. It can be made of plastic, metal, or any other rigid material. An example material is hardened titanium. FIG. 6(c) demonstrates an exemplary contour of male clasp end 214, while FIG. 6(d) demonstrates an exemplary contour rigid member 212. It should be readily understood that the exemplary contour of rigid member 212 renders it concave on an inner surface to be disposed toward an outer surface of an organ to be clamped, and convex on an outer surface for engagement with a spring component. However, other shapes may be used as desired.

Turning next to FIG. 7, and referring generally to FIGS. 7A-7D, another piece of the three-piece clamp can be a rigid member 216 having a female clasp end 218 that includes a hinged loop 220. As will be described further below with reference to FIG. 9, this rigid member 216 serves as one of the elongated members of the clamp for forming the partition that divides the stomach. It can be made of plastic, metal, or any other rigid material. An example material is hardened titanium. Similarly, the loop 220 can be made of various materials, an example of which is titanium wire.

Turning next to FIG. 8, and referring generally to FIGS. 8A-8D, a third piece of the three-piece clamp can be a spring member 222 having a slotted bight portion 224. As will be further described below with reference to FIG. 9, the spring member engages with the rigid members to form the clamp and provides the bight portion that permits formation of a passage between the two partitioned regions of the clamped stomach. It can be made of plastic, metal, or any other springy material. An example material is spring tempered titanium.

Turning now to FIG. 9, and referring generally to FIGS. 9A-9D, the three-piece clamp can be assembled by engaging the rigid members 212 and 216 to the spring member 222. For example, the rigid members can be welded or coupled to arms of spring member at various locations 226. In one embodiment, the rigid members 212 and 216 can be attached to interior surfaces of the arms of spring member 222, with the loop 220 arranged to hinge towards and engage the male clasp end 214 of the distal end of rigid member 212. Thus, the rigid members 212 and 216 are employed to form a partition, while the spring member 222 forms a passage between the partitioned regions of an organ or body as shown in FIG. 10. These rigid members 212 and 216 may be of non-uniform thickness to accommodate gradual closing of the clamp from the proximal end towards the distal end in such a manner that a non-uniform thickness of an organ, such as walls of a stomach, can be clamped without injury. Alternatively or additionally, sleeves of padding material can be slid over the arms of the clamp, and the padding material can be of non-uniform thickness as desired. It is envisioned that rigid members 212 and 216 and padding material of varying lengths, contours, and thicknesses may be provided to accommodate needs of different patients as desired.

Turning now to FIG. 10, some embodiments of the surgical clamp installation tool can be used to install the clamp 100 within an abdominal cavity in order to perform bariatric surgery. In particular, the clamp can be positioned, closed, and latched to partition the stomach into a small vertical pouch 500 and an excluded section 502. The vertical pouch 500 receives food at 504, but the food is not able to enter the excluded section 502. Using the installation tool 102 (or 202) to engage with the bight portion 106 of the clamp 100, the clamp 100 may be installed in a substantially vertical position on the stomach in one embodiment. That is, if the human patient having the clamp 100 installed were to stand upright, the longitudinal axis of the clamp 100 would be substantially parallel to the gravity vector. Thus, a passage forming section formed in the bottom of the stomach by the clamp allows gastric juices to flow at 506 from the excluded section 502 into the vertical pouch 500.

Turning to FIG. 11, a method for clamping an internal organ can include inserting a surgical clamp through an opening into a body of a living organism at block 150. Then the two elongated members of the surgical clamp are positioned on opposite sides of an internal organ of the living organism at block 152. At block 154, closing and latching the surgical clamp to partition a cavity inside the internal organ includes clamping the exterior of the internal organ with the two elongated members.

As mentioned above, the internal organ can be a human stomach. In this case, closing and latching the clamp can include installing the clamp in a substantially vertical or angled position with a passage forming section of the clamp located towards a bottom of the stomach. This positioning can create a small, vertical stomach pouch and thereby limit the intake of food into an excluded section or portion of the stomach, but still allow gastric juices from the excluded portion of the stomach to flow into the vertical stomach pouch. This partitioning can alter the production of hormones, enzymes and chemicals that affect metabolism, energy levels, hunger, digestion, and absorption of nutrients that are affected by exclusion of gastric fundus and body of the stomach by the partitioning. Sheathing the elongated members of the clamp in silicone padding material along a majority of their length is intended to reduce trauma and/or necrosis of the stomach or other internal organ and enable successful reversal of the surgery. Thus, the method can further include reversing the surgery by removing the clamp.

Inserting the surgical clamp can include performing natural orifice transluminal endoscopic surgery (NOTES). Alternatively, or additionally, it can include performing a combination of NOTES and an assistant trochar placed into an abdominal cavity. This combination can include two or more of a conventional, laparoscopic, NOTES, and one port technique. The NOTES technique can include at least one of transgastric, transvaginal, transrectal, transcolonic, or combinations thereof. The one port technique is used for the introduction of several instruments, and encompasses a one port abdominal (including umbilical), perineal, retroperitoneal approaches, or combinations thereof.

Turning to FIG. 12, a method for clamping an internal organ can include engaging a surgical clamp to a head of a surgical clamp installation tool at block 160. At block 162, the surgical clamp installation tool can be employed to close the clamp and insert the clamp through an opening in a body cavity of a living organism. Then the tool can be employed at block 164 to reopen the clamp and to position elongated members of the clamp on opposite sides of an internal organ within the body cavity. Next, at block 166, the tool can be employed to close the clamp upon the internal organ and thereby partition a cavity inside the internal organ. The limbs, arms, or elongated members of the clamp close in such a fashion as causing a gradual diminishing space between the two limbs, as the space opening extends proximally, accounting for the different thickness of the stomach. The clamp closes in a fashion that exerts enough pressure to maintain the opposite walls closed to each other without creating damage/trauma/ischemia to the stomach or other organ walls themselves. Then at block 168, the clamp can be latched to fix it in position to partition the internal organ and the cavity inside the internal organ. Also, at block 170, the clamp can be disengaged from the head of the surgical clamp installation tool, and the tool can be retracted from the body cavity at block 172. It is envisioned that the clamp may be configured to latch automatically when the clamp is fully closed. Alternatively, the tool may first be disengaged and removed, and the clamp subsequently latched using an additional tool. Moreover, additional steps may be employed to secure the clamp in place, such as using sutures.

As already described above, padding material can be employed on surfaces of the elongated members of the surgical clamp to reduce damage to the internal organ that would prevent reversal of the surgical procedure. In other embodiments, the thickness or surface contour of the elongated members or arms of the surgical clamp may be provided to align with the particular organ or body being clamped so as to provide the desired pressure or force at each location of the organ or body being clamped. Additionally, engaging the surgical clamp to the head of the surgical clamp installation tool may include passing a T-bar adjacent the end of a pull rod of the installation tool through a slotted aperture formed in a bight portion of the clamp, and rotating the T-bar using a lever or dial. Also, employing the surgical clamp installation tool to close and reopen the clamp may include operating a lever or trigger on a handle of the installation tool to pull and release the pull rod. Further, employing the surgical clamp installation tool to position the elongated members of the surgical clamp may include manipulating a dial on a handle of the installation tool to articulate the head from side to side in a desired plane(s).

Turning now to FIG. 13, another embodiment of a surgical clamp 600 and surgical installation tool 602 is similar in structure and function to those embodiments described above. One notable difference from the embodiments previously described is that the articulating head 604 of the surgical installation tool 602 is keyed with a curvature or radius configured to hold the clamp 600 securely in place while permitting the clamp 600 to remain in an open position. This configuration permits a surgeon holding the installation tool 602 in one hand to hold the clamp 600 securely in the articulating head 604 of the tool 602 while pressing the distal ends of the clamp 600 together with the other end for entry to a trochar. Once the distal ends of the clamp 600 have entered the trochar, the trochar then holds the ends shut, and permitting the surgeon free use of the other hand. Upon entry to the abdominal cavity, the clamp naturally springs open for engagement with a bodily organ, such as the stomach, and the surgeon can articulate the head from side to side while it is held securely in the head 604 while still in the open position. Once in position, the surgeon can close the clamp using sutures and/or by applying pressure externally or internally using other surgical tools. Thus, the installation tool 602 may not be employed to close the clamp on an internal organ of the patient, but may be employed to hold, insert, and articulate the clamp into position.

Referring now to FIG. 14, clamp 600 can have a three piece design similar to that described above. In other words, it can have a spring member 606 that is comprised predominantly of spring steel, and that is engaged with lower and upper rigid members 608 and 610. These rigid members 608 and 610 can be comprised primarily of titanium, and they can have a concavity that increases their rigidity. In addition, suture holes 612A-612E can be provided in upper rigid member 610, as well as in an upper portion of spring member 606. A surgeon can employ these suture holes 612 to secure the clamp 600 in place on a stomach or other bodily organ. It is envisioned that additional or alternative suture holes 612 can be provided, such as in lower rigid member 608 and lower portion of spring member 606, and that positions of the suture holes 612 can be different from those shown. However, as will be more fully described below with reference to FIGS. 19-27, the placement of suture holes in the upper rigid member 608 and upper portion of spring member 606 can permit suturing of the clamp 600 in place prior to application of a silicone sleeve (see FIGS. 19-27) that slides onto the clamp via the un-sutured lower rigid member 608 and lower portion of spring member 606. Yet, once the sleeve is installed, it should be understood that additional suture holes 612 provided in lower rigid member 608 and/or lower portion of spring member 606 may prove useful in a subsequent application of additional sutures.

Turning now to FIGS. 15(a)-15(f) and referring generally thereto, it should be appreciated that a double row of suture holes 612A-612H can be provided in spring member 606 and upper rigid member 610, a distal portion of which can exhibit a male clasp feature 614 positioned to engage a female clasp feature, such as a wire loop 616, of lower rigid member 608. Suture holes 612D and 612E can be positioned on spring member 606 at a location that lies between a position at which upper rigid member 610 is engaged to spring member 606, and a position at which a slot 618 is formed in a bight portion of spring member 606. In the case that the distal end of upper rigid member 610 exhibits a male clasp feature 614, such as a planular curvature away from a plane in which the upper rigid member 610 predominantly lies, a complimentary female clasp feature can be exhibited by a distal end of lower rigid member 608, such as the aforementioned rectangular wire loop 616 engaged by a hinge formation 620 provided in the distal end of lower rigid member 608. It should be readily understood that the same functionality can be achieved if upper rigid member 610 exhibits the female clasp feature, and lower rigid member 608 exhibits male clasp feature 614. Thus, the positions of the clasp features can be reversed in other embodiments.

Turning now to FIG. 16, another additional feature of clamp 600 can be a detent that is 622 formed in hinge formation 620, and that engages wire loop 616 of the female clasp feature. This detent 622 can be positioned on the hinge formation 620 at a location that is most distal when the clamp 600 is held in a closed position, and it can be sized and shaped to hold the wire loop 616 in a lowered position at which the loop 616 lies in a plane parallel to a plane in which lower rigid member 608 predominantly lies. A similar or identical detent (not shown) can be provided on an opposite side of hinge formation 620, and it can be similarly distally positioned to assist in holding the wire loop 616 in the aforementioned lowered position. This lowered position allows the clamp 600 to be inserted through a trochar and guided to enclose a bodily organ, such as a stomach, at which point the aforementioned silicone sleeve (see FIGS. 19-27) can be partially applied. Then, before the silicone sleeve is fully engaged to the clamp 600, wire loop 616 can be forced out of detent 622 into a raised position at which it engages the male clasp feature 614 of the clamp 600.

Before raising the wire loop 616, it is envisioned that the clamp 600 can be pressed into a closed position by use of two or more graspers inserted into the abdominal cavity through additional trochars (i.e., multiport technique). Then, a suture tag pre-applied to wire loop 616 can be used to force wire loop 616 out of detent 622 into the raised position, resulting in the wire loop 616 engaging the male clasp feature 614 and holding the clamp 600 in the closed position without assistance from the two or more graspers. Alternatively or additionally, it is envisioned that closing and latching of the clamp 600 can be achieved by utilizing any suitable endoscopic surgical tools and techniques as will be readily apparent to one skilled in the art from the present disclosure.

Turning now to FIGS. 17(a)-17(f) and referring generally thereto, an endoscopic surgical installation tool for engaging and manipulating the clamp can be similar to those described above. For example, the installation tool can have a handle 650, trigger 652, pull rod, T-bar 654, cylindrical tube 656, dial 658 (e.g., with thumb lever), hub, guidelines, and articulating head 604 that are identical or similar to those described above. However, as previously described, a curvature or incline imparted to the head 604 by wedges of the head 604 can be keyed to a bight portion of the previously described clamp so as to hold the clamp in a fully open or predominantly open position when T-bar 654 has been fully retracted by actuation of trigger 652. Additionally, a latch release 660 can be provided that can extend from both sides of handle 650 for ergonomic, ambidextrous operation.

Turning now to FIG. 17, the latch release 660 can have a hinged plate with a retention spring that forces the latch release 660 upwards to engage a latch 662 provided at a proximal end of pull rod 664. In use, a surgeon can engage the T-bar to the clamp 600 by rotating the clamp 600 and/or installation tool in a common longitudinal axis until the T-bar fits through the notch in the bight portion of the clamp 600, and then rotating the clamp 600 and/or installation tool an integer multiple of ninety degrees until a length direction of the T-Bar is perpendicular to a length direction of the notch. Then, actuation of trigger 652 can retract pull rod until opposing latch surfaces (e.g., edges, extensions, faces, flanges, gouges, hooks, inclines, ledges, lips, notches, overhangs, projections, protrusions, ribs, ridges, skirts, serrations, slits, slots, teeth, wedges, and combinations thereof) of the latch 662 and release 660 can catch and hold the pull rod 664 in a fully retracted or predominantly retracted position.

Once the latch 662 is engaged, the clamp 600 is ready to be inserted into an inflated abdominal cavity through a trochar as described above, and a seal provided between cylindrical tube 656 and clevis 668 can prevent out gassing from the abdominal cavity through the head 604 and/or cylindrical tube 656. Alternatively, the seal can be provided anywhere inside cylindrical tube 656. In some embodiments, the seal is achieved by using a circular silicone die having a slit and a hole in the middle, with the pull rod 664 threaded through the hole.

Once the clamp 600 is in position within the abdominal cavity to enclose and partition the stomach or other organ, pressing down on latch release 660 can permit automatic extension of pull rod 664 by action of a torsion spring provided to trigger screw 666 to force de-actuation of trigger 652. The T-bar can then be disengaged from the clamp by rotating the installation tool along its longitudinal axis an integer multiple of ninety degrees and removing it from the trochar. Thus, it should be apparent that, in some embodiments, the pull rod may not be configured to rotate as in alternative embodiments described above, but only to retract and to extend.

Turning now to FIG. 19, a silicone sleeve 700 can be configured to engage clamp 600. In some embodiments, silicone sleeve 700 can be formed to cover primarily an upper arm and both ends of clamp 600. This silicone sleeve 700 can be used as padding to protect surrounding organs from irritation or damage. Thickness of the silicone can be varied for different applications, such as partitioning an organ, stomach, or vessel.

Turning now to FIGS. 20-27 and referring generally thereto, the silicone sleeve 700 can have tubular section 702 at a proximal end that slides onto the lower arm of clamp and can be manipulated into position to encapsulate the previously described bight portion of the clamp. The clamp can then be closed and latched as described above. Presuming that the upper arm of the clamp has already been sutured to the organ, stomach, or vessel, a distal end of the sleeve 700 can then be engaged to encapsulate the distal end of the clamp. For this purpose, the distal end of the sleeve 700 can be configured as a latch cap 704 that is form fitted to the closed latch features (see FIG. 25). A padding strip 706 situated between the tubular section 702 and latch cap 704 can be sized to a length of the clamp so as to be stretched taught across the upper arm of the clamp once the sleeve 700 is installed. A slot engaging feature 708 formed inside of tubular section 702 can be provided to engage with the previously described slot in the bight portion of the clamp by plugging the slot, and thus hold the tubular section of the sleeve 700 in place on the bight portion of the clamp.

Turning now to FIG. 28, a method of performing surgery can begin at step 750 by engaging the previously described clamp to the previously described surgical installation tool in one or more of the previously described manners. Thereafter, the clamp can be inserted through a trochar at step 752, and positioned to enclose an organ (e.g., stomach, vessel, etc.) at step 754. Next, at step 756, an upper arm of the clamp can be sutured to the organ though suture holes supplied in the clamp as previously described, and the installation tool can be disengaged and removed from the trochar at step 758. Thereafter, the previously described silicone sleeve can be slid over a lower arm of the clamp at step 760 as previously described, and the clamp can be closed and latched at step 762. Finally, at step 764, a latch cap of the silicone sleeve can be fit over the latch of the clamp, and additional sutures can be applied if desired. It should be understood that the sequence of the aforementioned steps can vary in additional or alternative embodiments, and that additional or alternative steps can be employed as will be readily apparent to one skilled in the art.

A number of additional and alternative embodiments of the surgical clamp and installation tool can have characteristics that are different from those described above. For example, it is envisioned that a surgical clamp not intended for bariatric surgery might not have a passage forming section, and that such a clamp might be smaller or larger, depending on the purpose of the clamp. For example, the clamp can be one-tenth of an inch in length to partition a blood vessel, or twenty-two centimeters in length to partition a stomach. Moreover, the clamp can be configured to partition any internal organ, and can vary in length accordingly between these two example lengths, or be longer or shorter as required. Also, the guide members might have one or more protrusions aligned with the engagement feature and configured for insertion into the slot formed in the bight portion of the clamp. Moreover, it is envisioned that the installation tool can be integrated with an endoscope and/or surgical robot, and that appropriate robotic elements can be included in place of or in addition to those described above. These and other features can be included in various combinations without departing from the scope of the invention as defined in the following claims.

What is claimed is:

1. A surgical clamp comprising:
at least two elongated members each having an elongated length, wherein at least one surface of the at least two elongated members has a padding material positioned adjacent at least a portion of the surface;
a bight portion joining said two elongated members at a proximal end of the surgical clamp and biasing said two elongated members in an open position at a distal end of the surgical clamp, wherein said bight portion has an exterior surface, an interior surface, and at least one engagement feature provided therein, wherein the at least one engagement feature of the bight portion includes at least one opening formed in the bight portion, and wherein the at least one opening of the bight portion extends from the exterior surface to the interior surface; and
a clasp mechanism having a male component disposed on one of the two elongated members at the distal end of the surgical clamp and a female component disposed on the other of the two elongated members at the distal end of the surgical clamp.

2. The surgical clamp of claim 1, wherein the at least two elongated members are attached to elongated members of a spring component that serves as the bight portion.

3. The surgical clamp of claim 2, wherein the spring component includes steel.

4. The surgical clamp of claim 2, wherein the at least two elongated members of the surgical clamp are attached to interior surfaces of the elongated members of the spring component by welding.

5. The surgical clamp of claim 2, wherein the elongated members are comprised of titanium, and a surface of the at least two elongated members of the surgical clamp is curved and contacts at least one of the elongated members of the spring component.

6. The surgical clamp of claim 1, wherein spacing between the interior surfaces of said at least two elongated members includes a partition forming section located nearer the distal end of the surgical clamp than the proximal end of the surgical clamp, and a passage forming section located nearer the proximal end of the surgical clamp than the distal end of the surgical clamp.

7. The surgical clamp of claim 6, wherein the bight portion includes a spring portion that serves at least partially as the passage forming section.

8. The surgical clamp of claim 7, wherein said padding material is connected to at least one of the two elongated members at least at a location on the surface corresponding to at least part of the partition forming section.

9. The surgical clamp of claim 8, wherein the padding material is comprised predominantly of silicone.

10. The surgical clamp of claim 1, wherein the at least one opening formed in the bight portion comprises a slotted aperture having a width and a length, wherein the length is greater than the width.

11. The surgical clamp of claim 10, wherein the length of the slotted aperture is oriented perpendicular to a longitudinal axis of the surgical clamp.

12. The surgical clamp of claim 1, wherein the male component of the clasp mechanism corresponds to an end of the elongated member that flares away from a longitudinal axis of the surgical clamp when the surgical clamp is placed in a closed position.

13. The surgical clamp of claim 12, wherein the female component of the clasp mechanism corresponds to a loop disposed to engage the end of the elongated member when the surgical clamp is placed in the closed position, and a hinge formation engaging the loop has a detent distally positioned to retain the loop in a plane parallel to a plane in which a longitudinal axis of the clamp predominately lies when the clamp is closed.

* * * * *